United States Patent
Collins et al.

(10) Patent No.: US 11,524,289 B2
(45) Date of Patent: Dec. 13, 2022

(54) NANOSPLASH: A SALIVA-BASED DIAGNOSTIC FOR VIRAL INFECTION SUITABLE FOR HOME USE

(71) Applicant: CONDUIT, INC., Revere, MA (US)

(72) Inventors: Logan Thrasher Collins, Revere, MA (US); Ryan Robinson, Revere, MA (US)

(73) Assignee: Conduit Inc., Revere, MA (US)

( * ) Notice: Subject to any disclaimer, the term of this patent is extended or adjusted under 35 U.S.C. 154(b) by 0 days.

(21) Appl. No.: 17/539,019

(22) Filed: Nov. 30, 2021

(65) Prior Publication Data

US 2022/0168728 A1    Jun. 2, 2022

Related U.S. Application Data

(60) Provisional application No. 63/119,089, filed on Nov. 30, 2020.

(51) Int. Cl.
| | | |
|---|---|---|
| *B01L 3/00* | (2006.01) | |
| *G01N 33/53* | (2006.01) | |
| *C12Q 1/6834* | (2018.01) | |
| *C12Q 1/6853* | (2018.01) | |

(52) U.S. Cl.
CPC .......... *B01L 3/5027* (2013.01); *C12Q 1/6834* (2013.01); *C12Q 1/6853* (2013.01); *G01N 33/5308* (2013.01); *B01L 2300/04* (2013.01); *B01L 2300/0861* (2013.01)

(58) Field of Classification Search
CPC . C12Q 1/6834; C12Q 1/6853; B01L 2300/04; B01L 3/5027; B01L 2300/0861
See application file for complete search history.

(56) References Cited

U.S. PATENT DOCUMENTS

| | | | |
|---|---|---|---|
| 2011/0200983 A1* | 8/2011 | Smith | C12Q 1/705 435/5 |
| 2017/0026806 A1 | 9/2017 | Jampani et al. | |
| 2019/0200966 A1* | 7/2019 | Zhan | B01L 3/50 |

OTHER PUBLICATIONS

Davidson, Y., Immobilization of Enzymes on Porous Silica for the Micro-Digestion of Oligonucleotides With Analysis by CE, Louisiana State University, 2000, 144 pages.
International Search Report and Written Opinion for PCT/US2021/61268 dated May 5, 2022, 12 pages.

* cited by examiner

*Primary Examiner* — Joseph G. Dauner

(57) ABSTRACT

Provided herein are compositions and devices for diagnosing and treating a viral infection in a subject and/or detecting a viral nucleic acid in a sample. In one example, a sample is treated in a first chamber and the sample is flowed into a second chamber, where any pathogenic nucleic acid is detected by oligonucleotides that are specific to the pathogen under test. Further, the oligonucleotides comprise a cleavage site for a restriction enzyme in the second chamber, which cleaves oligonucleotide-pathogenic nucleic acid hybrid resulting in the exposure of an enzyme that was being held by the oligonucleotide to its substrate, which generates a colorimetric and/or another visual readout.

11 Claims, 9 Drawing Sheets

Specification includes a Sequence Listing.

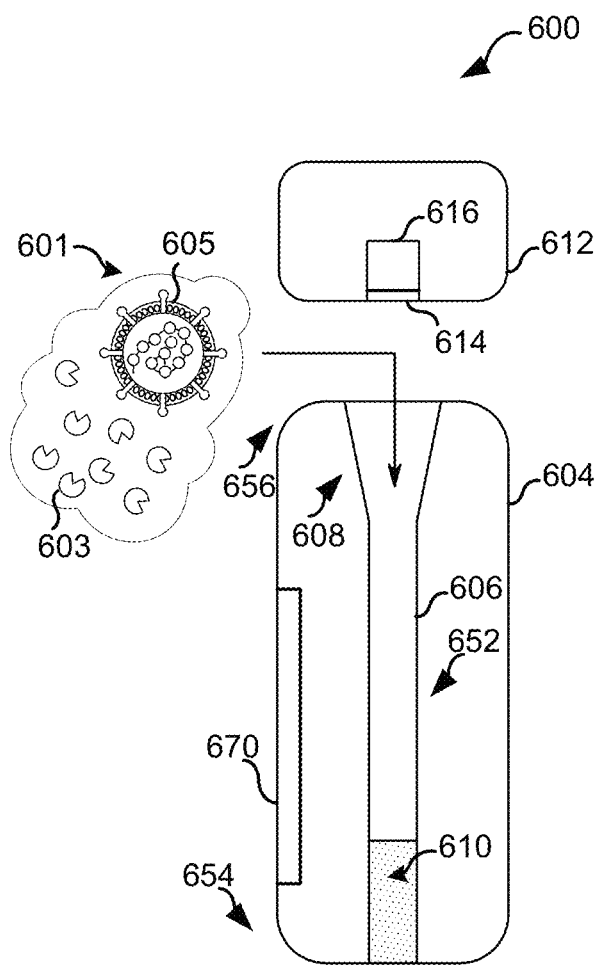 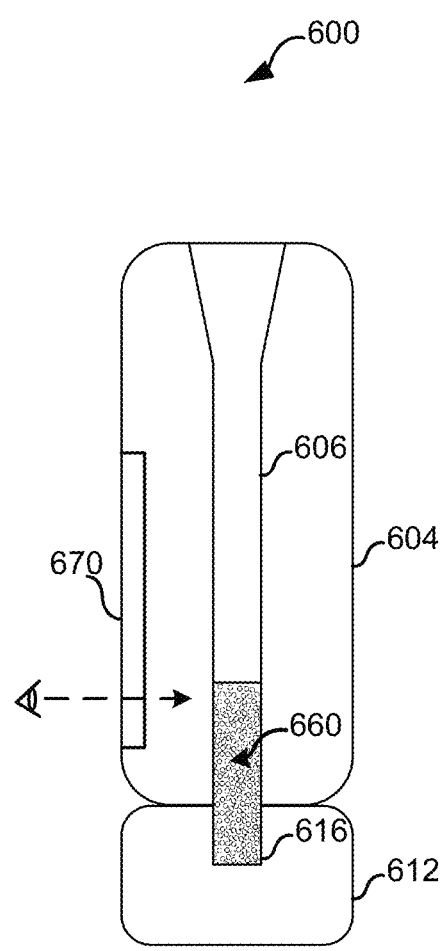
FIG. 6A  FIG. 6B

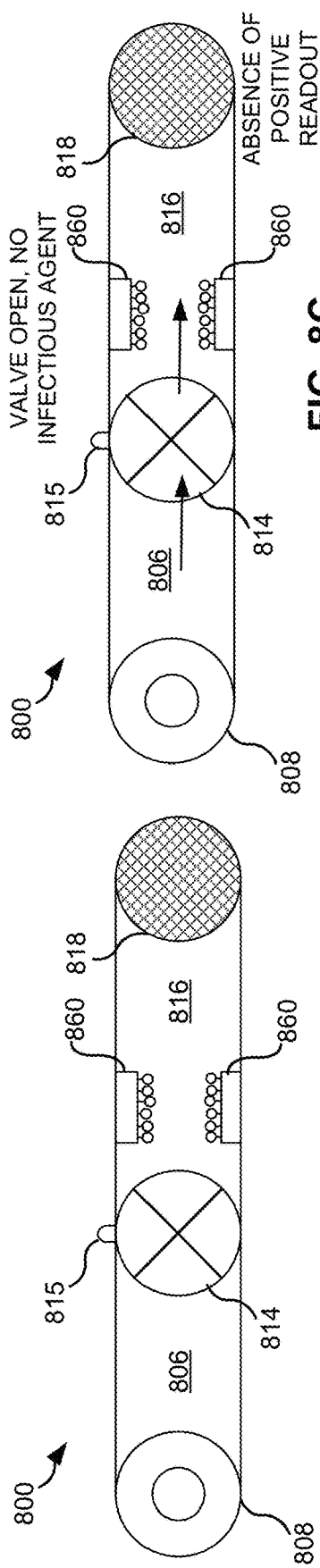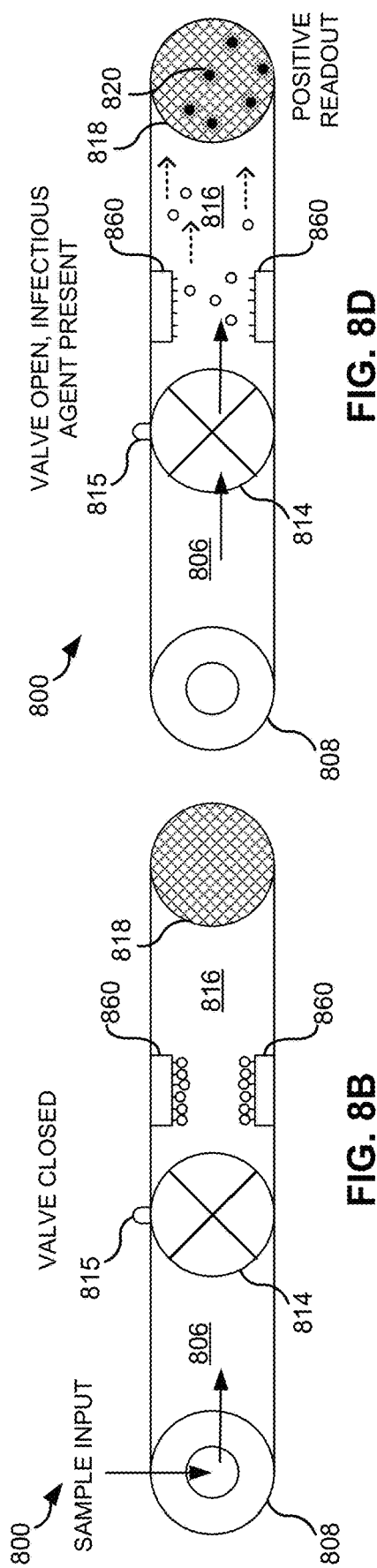

SEQUENCE LISTING

<160> NUMBER OF SEQ ID NOS: 16

<210> SEQ ID NO 1
<211> LENGTH: 113
<212> TYPE: DNA
<213> ORGANISM: Artificial Sequence
<220> FEATURE:
<223> OTHER INFORMATION: synthetic construct

<400> SEQUENCE: 1
acaggtacgt taatagttaa tagcgtactt cttttcttg ctttcgtggt attcttgcta      60
gttacactag ccatccttac tgcgcttcga ttgtgtgcgt actgctgcaa tat            113

<210> SEQ ID NO 2
<211> LENGTH: 113
<212> TYPE: DNA
<213> ORGANISM: Artificial Sequence
<220> FEATURE:
<223> OTHER INFORMATION: synthetic construct

<400> SEQUENCE: 2
atattgcagc agtacgcaca caatcgaagc gcagtaagga tggctagtgt aactagcaag    60
aataccacga aagcaagaaa aagaagtacg ctattaacta ttaacgtacc tgt           113

<210> SEQ ID NO 3
<211> LENGTH: 55
<212> TYPE: DNA
<213> ORGANISM: Artificial Sequence
<220> FEATURE:
<223> OTHER INFORMATION: synthetic construct

<400> SEQUENCE: 3
ctgttttcct tcaaggtcca taagaaaagg ctgagagaca tattcaaaag tgcaa          55

<210> SEQ ID NO 4
<211> LENGTH: 46
<212> TYPE: DNA
<213> ORGANISM: Artificial Sequence
<220> FEATURE:
<223> OTHER INFORMATION: synthetic construct

<400> SEQUENCE: 4
ctgttttcct tcaaggtcca taagaaaagg ctgagagaca tattca                   46

<210> SEQ ID NO 5
<211> LENGTH: 34
<212> TYPE: DNA
<213> ORGANISM: Artificial Sequence
<220> FEATURE:
<223> OTHER INFORMATION: synthetic construct

<400> SEQUENCE: 5
ctgttttcct tcaaggtcca taagaaaagg ctga                                34

<210> SEQ ID NO 6
<211> LENGTH: 55
<212> TYPE: DNA
<213> ORGANISM: Artificial Sequence
<220> FEATURE:
<223> OTHER INFORMATION: synthetic construct

<400> SEQUENCE: 6
ctgttttcct tcaaggtcca taagaaaagg ctgagagaca tattcaaaag tgcaa          55

<210> SEQ ID NO 7
<211> LENGTH: 46
<212> TYPE: DNA
<213> ORGANISM: Artificial Sequence
<220> FEATURE:
<223> OTHER INFORMATION: synthetic construct

<400> SEQUENCE: 7
ctgttttcct tcaaggtcca taagaaaagg ctgagagaca tattca                   46

<210> SEQ ID NO 8
<211> LENGTH: 34
<212> TYPE: DNA
<213> ORGANISM: Artificial Sequence
<220> FEATURE:
<223> OTHER INFORMATION: synthetic construct

<400> SEQUENCE: 8
ctgttttcct tcaaggtcca taagaaaagg ctga         34

<210> SEQ ID NO 9
<211> LENGTH: 56
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (7)..(7)
<223> OTHER INFORMATION: MethoxyethoxyCytosine
<220> FEATURE:
<221> NAME/KEY: modified_base
<222> LOCATION: (42)..(42)
<223> OTHER INFORMATION: MethoxyethoxyCytosine

<400> SEQUENCE: 9
ctgtttctcc ttcaaggtcc ataagaaaag gctgagagac acattcaaaa gtgcaa         56

<210> SEQ ID NO 10
<211> LENGTH: 59
<212> TYPE: DNA
<213> ORGANISM: Artificial Sequence
<220> FEATURE:
<223> OTHER INFORMATION: synthetic construct

<400> SEQUENCE: 10
cacaagacca tgttgacata ctaggacctc tttctgctca aactggaatt gccgtttta         59

<210> SEQ ID NO 11
<211> LENGTH: 47
<212> TYPE: DNA
<213> ORGANISM: Artificial Sequence
<220> FEATURE:
<223> OTHER INFORMATION: synthetic construct

<400> SEQUENCE: 11
cacaagacca tgttgacata ctaggacctc tttctgctca aactgga         47

<210> SEQ ID NO 12
<211> LENGTH: 38
<212> TYPE: DNA
<213> ORGANISM: Artificial Sequence
<220> FEATURE:
<223> OTHER INFORMATION: synthetic construct

<400> SEQUENCE: 12
caagaccatg ttgacatact aggacctctt tctgctca         38

<210> SEQ ID NO 13
<211> LENGTH: 59
<212> TYPE: DNA
<213> ORGANISM: Artificial Sequence
<220> FEATURE:
<223> OTHER INFORMATION: synthetic construct

<400> SEQUENCE: 13
cacaagacca tgttgacata ctaggacctc tttctgctca aactggaatt gccgtttta         59

<210> SEQ ID NO 14
<211> LENGTH: 47
<212> TYPE: DNA
<213> ORGANISM: Artificial Sequence
<220> FEATURE:
<223> OTHER INFORMATION: synthetic construct

```
<400> SEQUENCE: 14
cacaagacca tgttgacata ctaggacctc tttctgctca aactgga                47

<210> SEQ ID NO 15
<211> LENGTH: 38
<212> TYPE: DNA
<213> ORGANISM: Artificial Sequence
<220> FEATURE:
<223> OTHER INFORMATION: synthetic construct

<400> SEQUENCE: 15
caagaccatg ttgacatact aggacctctt tctgctca                           38

<210> SEQ ID NO 16
<211> LENGTH: 60
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (15)..(15)
<223> OTHER INFORMATION: MethoxyethoxyCytosine
<220> FEATURE:
<221> NAME/KEY: modified_base
<222> LOCATION: (50)..(50)
<223> OTHER INFORMATION: MethoxyethoxyCytosine

<400> SEQUENCE: 16
cacaagacca tgttcgacat actaggacct ctttctgctc aaactggaac tgccgtttta   60
```

NANOSPLASH: A SALIVA-BASED DIAGNOSTIC FOR VIRAL INFECTION SUITABLE FOR HOME USE

CROSS-REFERENCE TO RELATED APPLICATIONS

This application claims benefit under 35 U.S.C. § 119(e) of U.S. Provisional Application Nos. 63/119,089 filed Nov. 30, 2020, the contents of which are incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 30, 2021, is named 089974-000001US00_SL.txt and is 4 kilobytes in size.

TECHNICAL FIELD

The technology described herein relates to systems, methods, and compositions for diagnosing an infectious condition.

BACKGROUND

Infectious diseases, whether caused by ubiquitous and long-standing pathogens, emerging pathogens, or re-emerging pathogens, pose significant health and economic threats world-wide. As an example, the current outbreak of Covid-19 caused by the novel coronavirus severe acute respiratory syndrome (SARS) coronavirus 2 (SARS-CoV-2), continues to have devastating economic and humanitarian impact on a global scale. Rapid and reliable testing devices, which permit the user to detect symptomatic as well as asymptomatic infections, are of critical importance to mitigate the spread of infectious diseases. Further, the ability to effectively detect an infectious agent may assist individuals and communities in employing successful efforts, including quarantine, treatment, occupational health and safety, and contract tracing efforts.

SUMMARY

Devices, methods, compositions, and kits are provided for rapid and reliable detection of an infectious agent in a biological sample. A current standard used in testing for the presence of SARS-CoV-2 is based on reverse transcriptase-polymerase chain reaction (RT-PCR). However, RT-PCR based testing is conducted in centralized laboratories with expensive instrumentation and requires experienced personnel, and therefore cannot be employed outside well-equipped facilities. Further, RT-PCR relies on respiratory swab specimens (e.g., nasopharyngeal or oropharyngeal swabs, anterior nasal swabs, or mid-turbinate swabs) collected from an individual, which may not only discourage testing but also makes the RT-PCR based approach less effective for monitoring disease progression.

As alternatives to RT-PCR based testing, clustered regularly interspaced short palindromic repeats (CRISPR)-based approaches have been developed. Joung et al in N. Engl. J. Med. 383, 1492-1494 (2020) describe an example CRISPR-based Specific High Sensitivity Enzymatic Reporter unLocking (SHERLOCK) assay termed SHERLOCK testing in one pot (STOP). Therein, extraction of viral RNA is combined with isothermal amplification and CRISPR-mediated detection. However, the STOP assay described by Joung requires respiratory swabs and further, relies on isothermal amplification at optimum temperature, which requires running the test for at least 45 minutes. Taking into account the duration required for an individual to take a respiratory swab sample at home, the duration of amplification, and the narrow operation temperature of the amplification enzymes, the assay lacks efficiency and speed required for at-home testing.

Some testing approaches are based on loop-mediated isothermal amplification (LAMP) at a constant temperature. An example LAMP-based approach is described by Wei et al in a publication titled "Field-deployable, rapid diagnostic testing of saliva samples for SARS-CoV-2", medRxiv 2020.06.13.2012984. Therein, using a heat block, SARS-CoV-2 is detected in 30 minutes. However, Wei's approach is not conducive for at home testing due to requirement of heat blocks that can maintain constant temperatures for at least 30 minutes. In addition to the above drawbacks, the LAMP-based approach suffers from low sensitivity and specificity.

Lateral flow immunoassays (LFIAs) are another type of diagnostic for viral infection. Some LFIAs use immobilized antibodies which bind to target antigens while others employ immobilized antigens which recruit patient antibodies. LFIAs are more portable, easier to use, and give faster results than RT-PCR. However, LFIAs are also less sensitive and less accurate than RT-PCR. As a consequence, LFIAs have so far seen lesser utility during the COVID-19 pandemic than RT-PCR methods. There remains a need for new viral diagnostic options that are sensitive, accurate, fast, portable and which people can utilize at home.

In order to at least partially address the above-mentioned disadvantages, the inventors herein have developed devices, methods, and compositions for rapid and reliable testing that be performed efficiently and quickly at home. In one example, a device for detecting an infectious agent in a sample comprises: a first device housing including a first chamber, the first chamber including a first solution for releasing a nucleic acid of the infectious agent; a second device housing including a second chamber, the second chamber comprising a nucleic acid capture portion, a read-out generation portion, and second solution including at least one restriction endonuclease enzyme; wherein the nucleic acid capture portion comprises one or more layers of enzyme conjugated beads, each enzyme conjugated bead attached to the second chamber via a single stranded oligonucleotide; and wherein the single stranded oligonucleotide comprises a first sequence corresponding to a restriction site of the at least one restriction enzyme and a second sequence complementary to a fragment of the nucleic acid of the infectious agent.

In this way, the device enables a nucleic acid based testing approach for an infectious agent without tedious nucleic acid extraction or amplification steps. As a result, testing for the presence of the infectious agent can be performed with improved speed and efficiency in point-of-care settings or at home. Further, the device may detect infectious agents in a fluid sample, such as saliva, which reduces the discomfort and time required for acquiring respiratory swab sample.

As an example, the inventors have recognized that nucleic acids of infectious agents (e.g., viral nucleic acids) can be detected in a liquid sample by using a single stranded oligonucleotide linker that has sequence complementary to a target sequence in the nucleic acid of the infectious agent under investigation and including at least one restriction site in the sequence. The single stranded oligonucleotide linker attaches enzyme coated beads to walls of a chamber in the device. When viral particles are present in the saliva, the viral nucleic acid hybridizes with the single stranded oligonucleotide due to sequence complementarity. The hybridization generates a DNA/RNA heteroduplex responsive to which a restriction enzyme causes a restriction-enzyme mediated cleavage of the DNA/RNA heteroduplexes that form in the presence of the viral RNA, thereby releasing the enzyme coated beads into the solution. The enzyme coated beads then travel to a polymeric disk that includes a substrate for the enzyme. When the enzyme coated beads contact the substrate, the enzymatic reaction provides a visual change (e.g., colorimetric change, turbidimetric change, etc.) which can be readily detected by the user.

In this way, by using a unique nucleic acid capture and detection platform that is based on restriction enzyme mediated cleavage, infectious agents can be detected with improved speed and efficiency, and can be used in a wide range of settings including at-home testing, point-of-care testing, field testing, population testing, etc.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

A BRIEF DESCRIPTION OF THE DRAWINGS

In order to describe the manner in which the above-recited disclosure and its advantages and features can be obtained, a more particular description of the principles described above will be rendered by reference to specific examples illustrated in the appended drawings. These drawings depict only example aspects of the disclosure, and are therefore not to be considered as limiting of its scope. These principles are described and explained with additional specificity and detail through the use of the following drawings:

FIG. 6A shows a schematic illustration of an example device with a first chamber and a second chamber for detecting the presence or absence of an infectious agent, according to an embodiment of the disclosure;

FIG. 6B shows a schematic illustration of the device of FIG. 6A with the second chamber fluidly coupled with the first chamber, according to an embodiment of the disclosure;

FIG. 8A shows a schematic illustration of an example device for detecting the presence or absence of an infectious agent, according to an embodiment of the disclosure;

FIG. 8B shows a schematic illustration of an example sample collection via the device of FIG. 8A;

FIG. 8C shows a schematic illustration of an example negative result readout in the device of FIG. 8A;

FIG. 8D shows a schematic illustration of an example positive result readout in the device of FIG. 8A.

DETAILED DESCRIPTION

Described herein are devices, methods, compositions, and kits that permit rapid, low-cost detection of an infectious agent via nucleic acid targets (e.g., those specific to the infectious agent) in point-of-care conditions, for example, without access to refrigeration, laboratory equipment, or even on-scene medical professionals. The devices, methods, compositions, and kits described herein may be used with any bodily fluid type and may be configured to detect any known microorganism. Further, devices, methods, compositions, and kits described herein greatly improve efficiency in sample collection, sample preparation, and detection. Furthermore, the devices, methods, compositions, and kits greatly improve ease of use and speed of detection (e.g., from start of sample collection to determining the outcome).

Overview

Rapid and reliable at-home testing devices are key to reducing the spread of infectious diseases. Current approaches rely on RT-PCR assays for diagnosing infectious diseases, such as COVID-19. However, RT-PCR requires long processing times and cannot be performed by patients at home. In the case of the COVID-19 pandemic, this limitation has slowed down the responses of medical communities. Other alternatives, such as LFIA, LAMP-based assays, CRISPR-based assays, etc., are less sensitive and less accurate than RT-PCR. There remains a need for a testing device that is sensitive, accurate, fast, portable and which people can utilize at home.

Figures 1A, 1B:
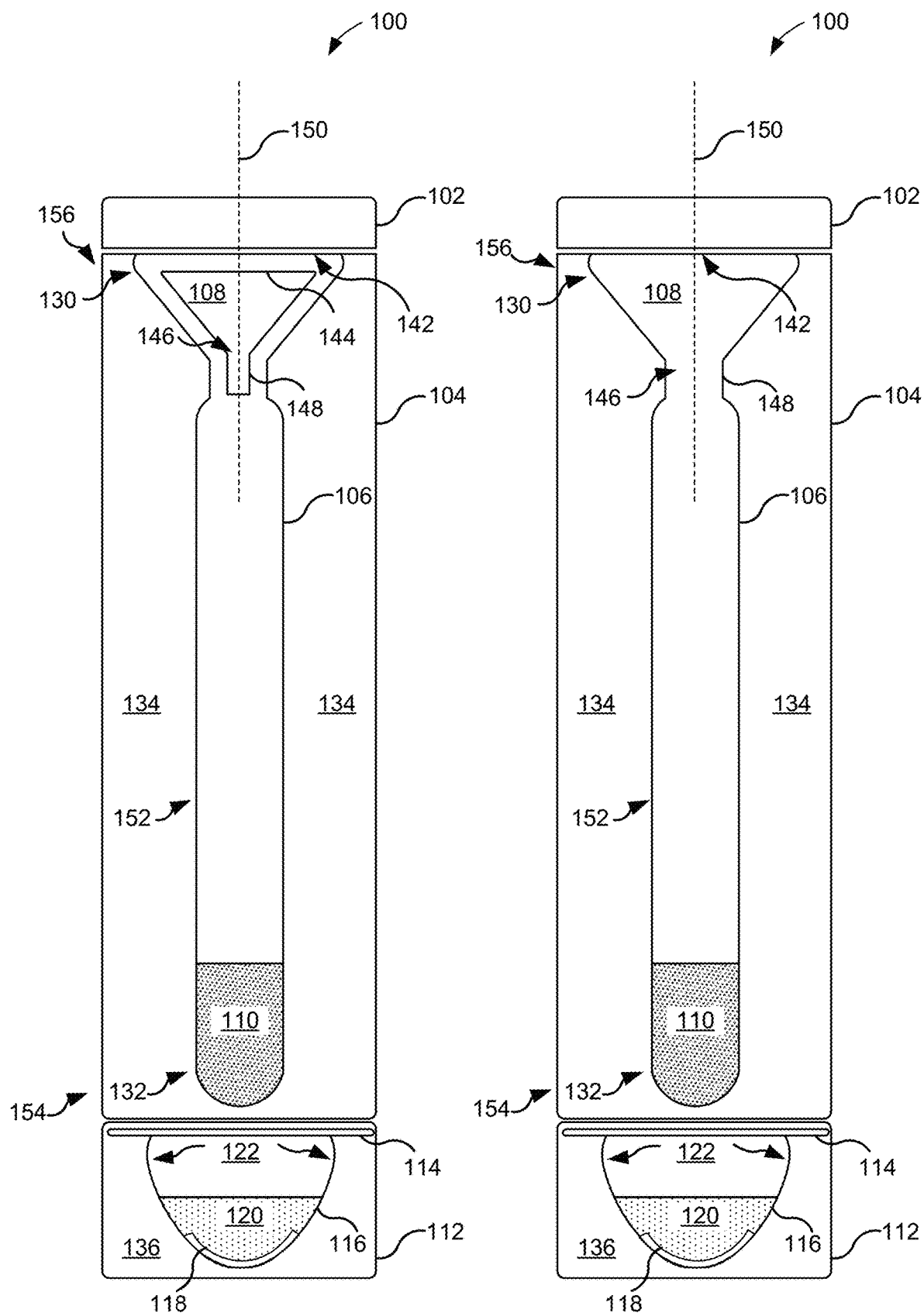
FIGS. 1A and 1B show schematic illustrations of different embodiments of a device for detecting the presence or absence of an infectious agent in a sample, according to an embodiment of the disclosure.

The inventors herein have developed devices, kits, compositions, and methods to rapidly detect target nucleic acids of infectious agents, based on a restriction enzyme based nucleic acid assay. Embodiments of a device that may be used for testing the presence or absence of an infectious agent in a sample is shown at FIGS. 1A and 1B. Further, various embodiments of the device are shown and described with respect to FIG. 2-FIG. 8A-8D. The device comprises a first chamber for efficiently and safely receiving and treating the sample (e.g., to neutralize DNases and RNases in the sample, and release nucleic acid of the infectious agent, if present). Further, the device includes a detection chamber (alternatively referred to herein as second chamber) which includes a nucleic acid detection portion that includes enzyme-conjugated microbeads covalently linked to a solid substrate (which may be the walls of the detection chamber) using single stranded DNA oligomers. The single stranded DNA oligomer comprises a recognition sequence that is complementary to a target nucleic acid of the infectious agent that is desired to be detected. In addition to the complementarity to the target nucleic acid, the recognition sequence also includes one or more restriction sites. If the infectious agent is present in the sample, the target nucleic acid hybridizes to the ssDNAs which connect the beads to the solid substrate. A restriction enzyme that recognizes the restriction sites is also included in the detection chamber. The restriction enzyme cleaves the hybrid (but not the ssDNA that is not hybridized). Once cleaved, the beads may freely diffuse away from the solid substrate, and may be detected via a suitable substrate for the enzyme on the beads. Further, the device is configured such that sample collection and detection can be performed seamlessly and rapidly using a single device. An example method for detection is described at FIG. 9.

In this way, the devices, compositions, and methods described herein provide significant improvement in the field of infectious disease diagnostics.

Device

Referring to FIGS. 1A and 1B, the figures show schematic illustrations of a first embodiment and a second embodiment of an example device 100 for detecting the presence of an infectious agent in a sample. In particular, the device 100 may be used for sensing the presence of an analyte (e.g., nucleic acid of the infectious agent) in the sample and generating a visual output indicative of the presence of the infectious agent. In one example, the sample may be a bodily fluid, such as saliva, blood, urine, mucus, tears, sweat, serum, mucus, amniotic fluid, breast milk, etc. The sample may also be a mixture of two or more bodily fluids. Accordingly, the device 100 may be used to detect presence of an infectious agent in a bodily fluid obtained directly from a patient without pre-processing such as nucleic acid extraction or amplification.

Device 100 includes a primary chamber 106 disposed in a first device housing 104 for receiving the sample and preparing the sample for subsequent detection. The primary chamber 106 includes an opening 142 at its proximal end 130 and is closed at the bottom at its distal end 132. The primary chamber 106 includes a receiving chamber 108 for receiving a sample from a subject. The receiving chamber 108 may be configured in a shape that facilitates direct sample collection from the subject without spilling. Further, the receiving chamber 108 may be configured to improve flow of the fluid sample into the primary chamber 106. In one example, as shown at FIG. 1A, the receiving chamber 108 has an inverted cone shape with a wide open base 144 at the top and a narrow opening 146 at the bottom. Further, the receiving portion 108 may have a tubular stem 148 extending from the bottom and into a collection chamber 152 to direct flow of the fluid sample into the collection chamber 152 of the primary chamber 106. In the illustrated example at FIG. 1A, the receiving chamber 108 is shown recessed within the primary chamber 106 and as a separate unit positioned within the primary chamber 106 with the stem 148 ending into the upper portion of the collection chamber 152. That is, the stem 148 may continue downward from the narrow opening 146 parallel to the vertical axis 150 and extend into the upper portion of the collection chamber 152 of the primary chamber 106. In some examples, the stem 150 may be slightly angled with respect to the vertical axis 150, such that a portion of the end of the stem is closer or touching an inner wall of the collection chamber 152. Thus, the sample may flow via the stem 148 and into the collection chamber along the walls of the collection chamber. In another embodiment, as shown at FIG. 1B, the receiving chamber 108 and the collection chamber 152 may be configured such that a distal edge (distal edge facing the collection chamber) of the tubular stem 148 of the receiving chamber 108 is directly coupled to a proximal edge of the collection chamber (proximal to the tubular stem 148).

In some embodiments, the stem 148 may include a one-way valve that allows flow of sample into the collection chamber 152 but not backwards into the receiving chamber, thereby improving safety when handling infectious samples.

Referring to FIGS. 1A and 1B, the narrow opening 146 is centered with respect to the base 144. That is, a vertical axis 150 of the passing through a center of the narrow opening 146 also passes through a center of the wide open base 144. However, in other examples, the narrow opening 146 may be oblique with respect to the base 144. That is, the vertical axis 150 passing through the center of the narrow opening does not pass through the center of the wide open base 146. Accordingly, the receiving chamber 108 may have an oblique inverted conical shape. An example of a receiving chamber that is shaped as an oblique inverted cone is shown and described below with respect to FIG. 3D.

The collection portion 152 of the primary chamber 106 includes a first solution 110. The first solution 110 may be used for deactivating deoxyribonuclease (DNase), Ribonuclease (RNase), and proteins that may be present in the sample, and further, the first solution may be used for disrupting the cellular structure of the infectious agent (e.g., nucleocapsid proteins of a virus) present in the sample and release the nucleic acid genome of the infectious agent. The solution containing the released nucleic acid genome is then flowed to a second chamber, for detection and a visual output (e.g., colorimeteric, turbidimetric output) indicating presence of the infectious agent, as discussed further below.

The first solution 110 comprises one or more protein deactivating enzymes (e.g., Proteinase K to deactivate DNases and RNases) and/or one or more ribonuclease (RNase) deactivating substances (e.g., Diethyl pyrocarbonate (DEPC)). Further, in some examples, the first solution 110 may include antimicrobial peptides derived from synthetic or natural resources for cell lysis and release of nucleic acid from the infectious agent in the sample. The antimicrobial peptides may increase membrane permeability, cell membrane lysis, and facilitate release of intracellular contents of the infectious agent. Example antimicrobial peptides include, but not limited to melittins, cathelicidins, and defensins.

In some examples, in addition to or alternative to antimicrobial peptides, depending on the cell type of the infectious agents (e.g., bacteria, virus, or fungi, or combinations thereof), one or more additional buffers may be used. As an example, the first solution 110 may comprise a lysis buffer, e.g., a cell lysis buffer. Suitable lysis buffers for various cell types are known in the art and commercially available. As a non-limiting example, a suitable lysis buffer can comprise a detergent and a buffer molecule(s). For example, an exemplary cell lysis buffer can comprise SDS (e.g., 10% SDS), Tris-HCl (e.g., at 1 M, pH 8.1), and EDTA (e.g., at 0.5 M, pH 8). Additionally, one or more nucleic acid stabilization agents and/or pathogen deactivation substances may be used.

Further, the primary chamber 106 may be positioned annularly within the first device housing 104, wherein the walls of the first device housing 104 and the walls of the primary chamber 106 are separated by a space 134. In some examples, one or more heating components may be positioned between the inner wall of the first device housing 104 and outer surface the primary chamber 106. For example, a heating sleeve (not shown) may cover the collection chamber 152 to heat the components in the collection chamber to a desired temperature for optimal enzymatic activity. As one non-limiting example, the heating sleeve may include one or more substances that may be activated (e.g., manually activated with pressure) to generate heat (e.g., via an exothermic reaction) to increase temperature to a range within an optimal operating range for a restriction enzyme that is used during detection. In another example, the sleeve may include electrical heating elements, such as a printed circuit board (PCB) heating element, coupled to a power source to heat the collection tube to a desired temperature. Additionally, one or more temperature sensors may be positioned at the collection chamber or integrated with the PCB heating element to generate a temperature readout and maintain the desired temperature for a desired duration (e.g., responsive to a user turning on a power on/off switch).

In some examples, as shown in FIGS. 1A and 1B, the collection chamber 152 may be centrally positioned within the first device housing such that a longitudinal axis of the collection chamber 152 aligns with a longitudinal axis of the first device housing 104. That is, when viewed from bottom, a center of the collection chamber 152 coincides with a center of the first device housing. In some other examples, the collection chamber 152 may be offset from the center of the first device housing 104 such that the longitudinal axis of the collection chamber 154 is parallel to and offset from the longitudinal axis of the first device housing 104. Thus, when viewed from the bottom, the center of the collection chamber 154 is offset from the center of the first device housing. FIGS. 3A-3D show different views of an example first device housing where the collection chamber is positioned offset from the center of the first device housing.

The device 100 further includes a second device housing 112 comprising a second chamber 116 for detecting presence of an infectious agent in the sample that has been treated in the collection chamber 152 (that is, treated with first solution 110 to release the nucleic acid genome of the infectious agent) and for generating a visual indication in response to detecting the presence of the infectious agent. The second chamber 116 includes a bottom indicator portion 118 (also referred to herein as a read-out generation portion) and a side nucleic acid capture portion (not shown) embedded on the inner walls 122 of an upper portion of the second chamber 116. Details of the nucleic acid capture portion will be described with respect to FIGS. 7A-7C. Briefly, the nucleic acid capture portion includes a pathogen specific single-stranded nucleic acid molecule (ss-nucleic acid). The pathogen specific ss-nucleic acid is an oligonucleotide that is complementary to a portion of a genomic nucleic acid of a target pathogen, which is desired to be detected. Further, the pathogen specific ss-nucleic acid molecule includes at least one shorter sequence that is recognizable by a restriction endonuclease. The pathogen specific ss-nucleic acid molecule is covalently bonded to the inner walls 122 of the second chamber at one end, and at another end, the pathogen specific ss-nucleic acid sequence is covalently coupled to a readout molecule. An example readout molecule may include a bead (e.g., magnetic beads) coated with an enzyme (e.g., galactosidase, peroxidase, catalase, etc.). When the nucleic acid genome released from the infectious particles are flowed into the second chamber 116 (or vice-versa), they are captured at the nucleic acid capture portion by the pathogen specific complementary portion. That is, the pathogen specific ss-nucleic acid portion hybridizes with the complementary portion of the nucleic acid genome of the infectious agent. A restriction endonuclease that is included in a second solution 120 in the second chamber 116 recognizes the restriction endonuclease-specific cleavage site in the hybrid. The restriction endonuclease then cleaves the hybrid (pathogen specific ss-nucleic acid and the infectious agent nucleic acid hybrid) at the cleavage site releasing the readout molecule. The readout molecules released from the walls 122 of the second chamber 116 are then free to interact with the bottom indicator portion 118. The bottom indicator portion 118 includes a substrate for an enzyme of the readout molecule (e.g., the enzyme coated on the beads). Responsive to readout molecules contacting the substrate on the bottom indicator portion 118, a visual output (color change, generation of foam, etc.) is generated, which is visible to the user (e.g., via a transparent window).

The second solution 120 includes a restriction endonuclease that specifically recognizes and cleaves at the cleavage site generated by hybridization of a portion of the nucleic acid genome of the infectious agent with pathogen specific ss-nucleic acid. The second solution 120 further includes a proteinase inhibitor to deactivate any proteinase that may be in the solution flowed from the collection chamber 152.

Further, the second device housing 112 includes a breakable seal 114 sealing an entirety of the top opening of the second chamber 116 in order to prevent the second solution from spilling out of the second chamber 116 during storage and transportation. During sample collection (via the receiving chamber) and sample treatment (within the collection chamber 152) using the solution 110, the second device housing 112 is not attached with the first device housing 104. That is, the second device housing 112 and the primary body remain un-coupled during storage, transportation, sample collection, and treatment with solution 110. The second device housing 112 is then coupled to the primary body during a detection phase after the treatment of the sample with the solution 110 in the collection chamber 152. In one example, as shown at FIGS. 1A and 1B, the second device housing 112 is configured as a cap. In one example, the cap may be screwed onto a distal end 154 of the first device housing when it is desired to generate a read-out. The screwing or twisting motion may break the breakable seal 114 as well as a portion of the distal end 132 of the primary chamber 106 causing the sample and the solution 110 in the collection chamber 152 of the primary chamber 106 to merge with the solution 120 in the second chamber 116. In this way, the genomic nucleic acid of the infectious agent that is lysed and released in the collection chamber 152 (using solution 110) is exposed to the nucleic acid capture portion in the second chamber 116 and detected via the bottom indicator portion 118.

In some examples, the second device housing 112 may be attached to a different part of the first housing 104 prior to use. For instance, the second device housing 112 may be configured such that the housing 112 may be coupled (e.g., as a cap that can be screwed on) to the first housing 104 either at the proximal end 156 or the distal end 154. Prior to use, the second device housing 112 may be coupled to the proximal end 156 (e.g., during storage, transport, etc.). When in use, a user may detach the second housing 112 to access the receiving chamber 108 and input the bodily fluid into the receiving chamber (e.g., provide spit into the receiving chamber if saliva is used as the sample). At this time, during sample collection, and further, for a threshold duration when the sample is mixed and incubated with the solution 110 in the collection chamber 152 (that is, during sample preparation when sample DNase and RNase are deactivated and the genome nucleic acid of the infectious agent is being released into solution), the second device housing 112 may remain detached from the first device housing 104. After the threshold duration, during detection phase, the second device housing 112 is coupled to the distal portion 154 of the first device housing 104. The coupling ruptures or breaks the distal end 132 of the collection chamber 152 as well as the openable seal 114 of the second device housing 112. For example, coupling mechanism is configured to break or open or rupture a distal portion of the collection chamber as well as the openable seal 114. As one non-limiting example, the second device housing 112 may be configured as a screw cap that when screwed to the first device housing at the distal end 154 causes the distal portion of the collection chamber 152 and the openable seal 114 to break or open or rupture.

Responsive to the second device housing 112 being coupled to the first device housing and the distal portion of the collection chamber as well as the openable seal 114 opened or ruptured or broken, the solution 110 and the (processed) sample merge with the second solution 120 in the second chamber. If the sample includes the infectious agent to be detected, the genomic nucleic acid of the infectious agent is captured at the nucleic acid capture portion and detected via the detection portion 118 in the second chamber 116 within the second housing 112.

In some examples, the visual output may be visible via one or more transparent windows (not shown) on the first device housing 104 and/or the second device housing.

The first device housing 104 may further include a proximal removable cap 102 coupled to a proximal portion 156 of the first device housing. The removable cap 102 may be removed prior to receiving the sample from the subject.

While the examples illustrated at FIGS. 1A and 1B show the second chamber 116 housed in the second device housing 112 that is coupled to the first device housing during the detection phase, in some examples, the primary chamber 106 and the second chamber 116 may be positioned within a single housing. An example device including a primary chamber and a second chamber in a single housing is shown and described with respect to FIGS. 8A-8D.

Figure 2:
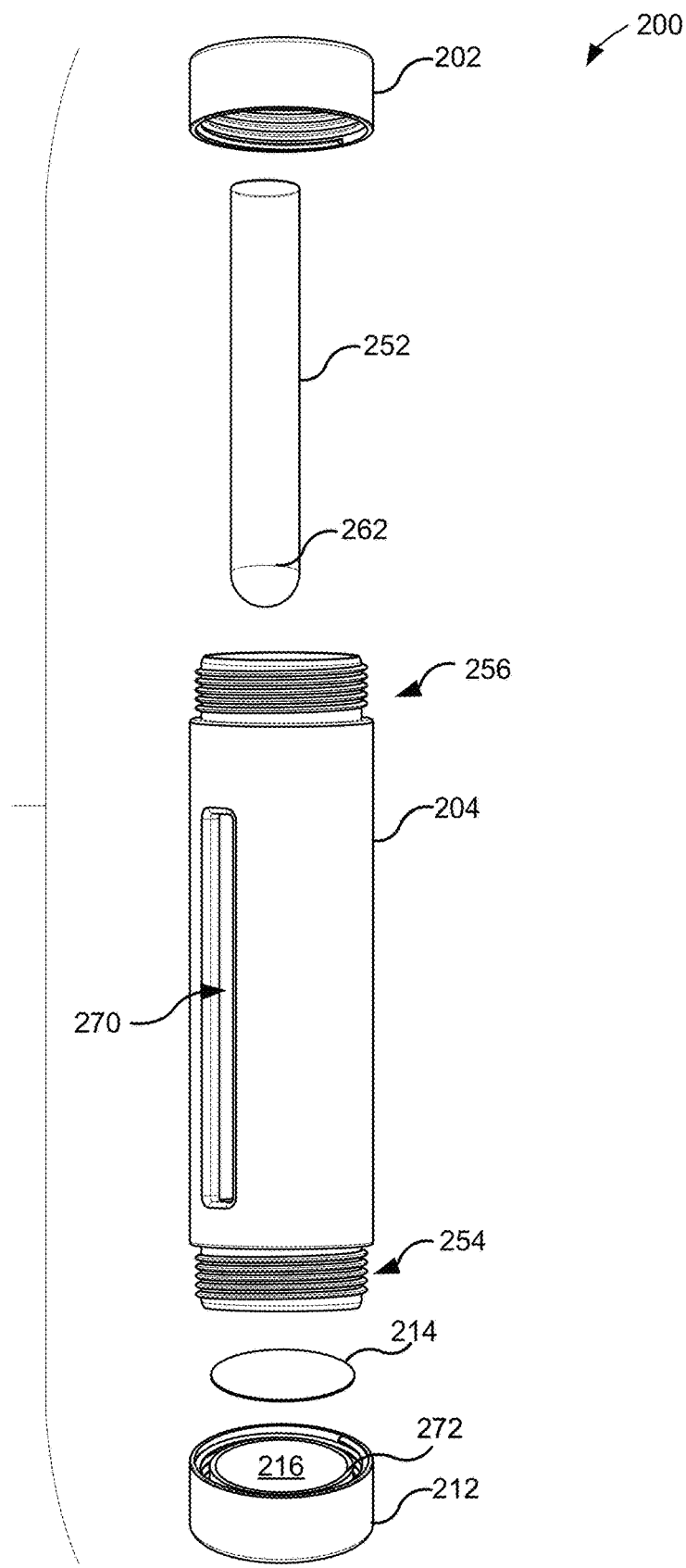
FIG. 2 shows an exploded view of an example device for detecting the presence or absence of an infectious agent in a sample, according to an embodiment of the disclosure.

Turning to FIG. 2, it shows an exploded view of an example device 200 for detecting the presence of an infectious agent in a sample, according to an embodiment of the disclosure. The device 200 is an embodiment of device 100 discussed above at FIGS. 1A and 1B. Accordingly, similarly named components have similar functions. Further, elements numbered 202, 204, 252, 254, 256, 212, and 214 in FIG. 2 correspond to elements numbered 102, 104, 152, 154, 156, 112, and 114 in FIG. 1.

Similar to device 100, the device 200 may enable easy handling and quick detection of an infectious agent, and may be deployed for testing for the presence of infectious agent in a variety of settings, including at-home use, in a health care environment, at businesses, workplace, travel checkpoints, etc. Further the device is easily scalable and may be deployed in a large scale (e.g., communities, airports) for testing large populations. Further still, the device may be adapted for testing any infectious pathogen that is detectable in a bodily fluid, without extensive preprocessing (e.g., nucleic acid extraction, amplification, etc.) and without requirement of heat-blocks or laboratory equipment.

The device 200 includes a first device housing 204 having a proximal end 256 and a distal end 254. The first device housing 204 includes a collection chamber 252 comprising a first solution within for deactivating RNases, DNases, and releasing genomic nucleic acid of the infectious agent in the sample. The sample may be received via a receiving chamber (shown in FIG. 3D) and collected in the collection chamber 252 which includes the first solution. The collection chamber 252 is configured as a test tube in this example and may include a scoring element 262 to facilitate breakage of the distal portion of collection chamber 252 to release the contents of the collection chamber during detection.

Figure 3C:
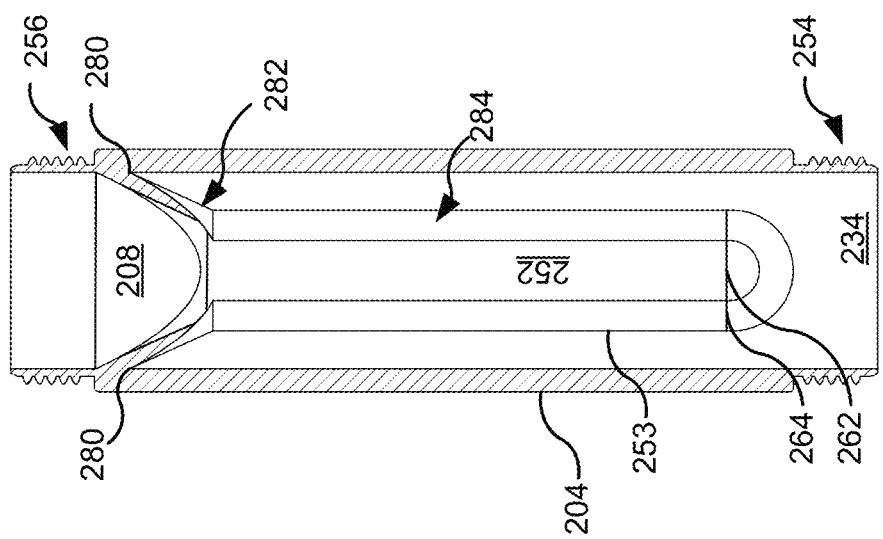
FIG. 3C shows a cross-sectional view taken along A-A' plane at FIG. 3B.
Figure 3B:
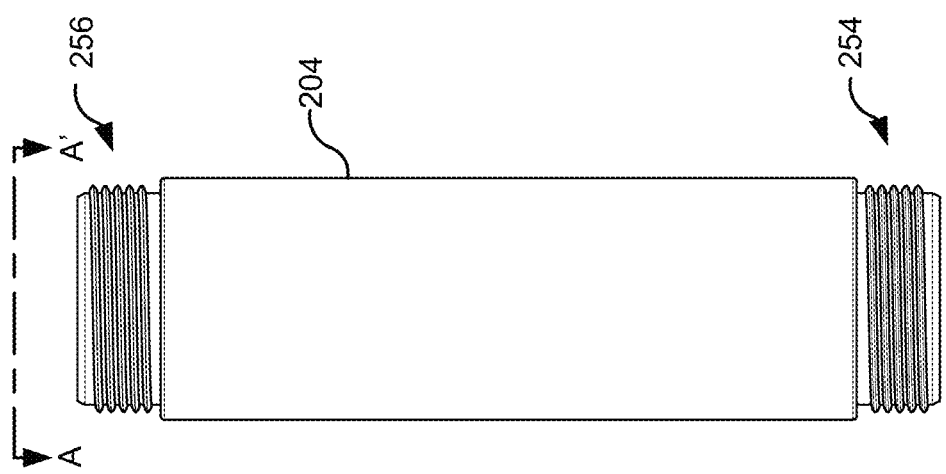
FIG. 3B shows a back view of the first device housing of the device of FIG. 2.
Figure 3A:
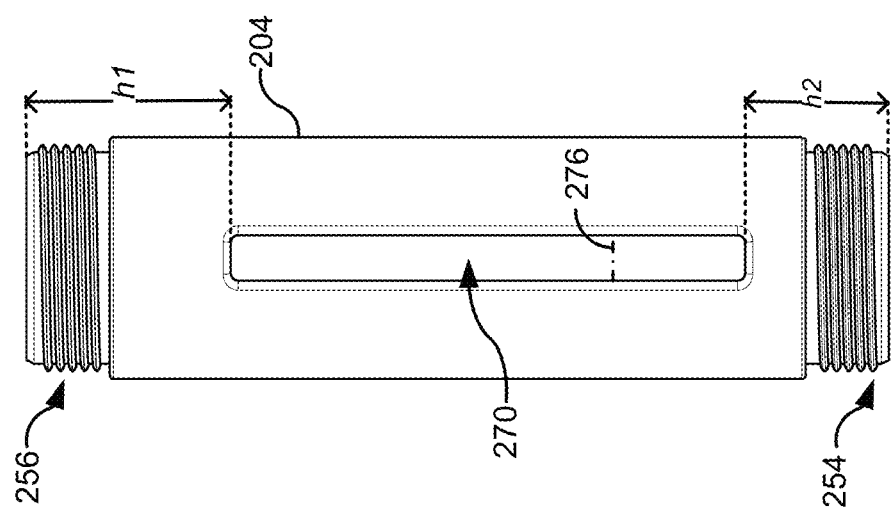
FIG. 3A shows a front view of a first device housing of the device of FIG. 2.
Figure 3D:
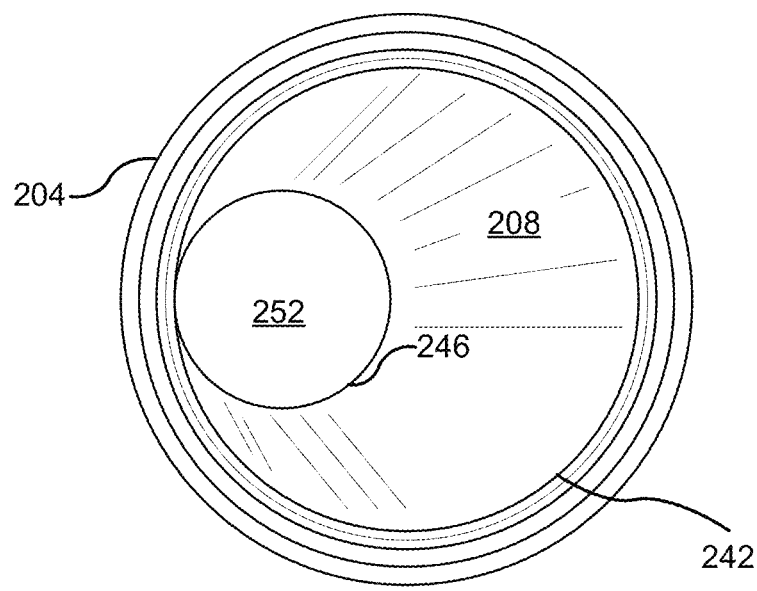
FIG. 3D shows a top view of the first device housing of the device of FIG. 2.
Figure 3E:
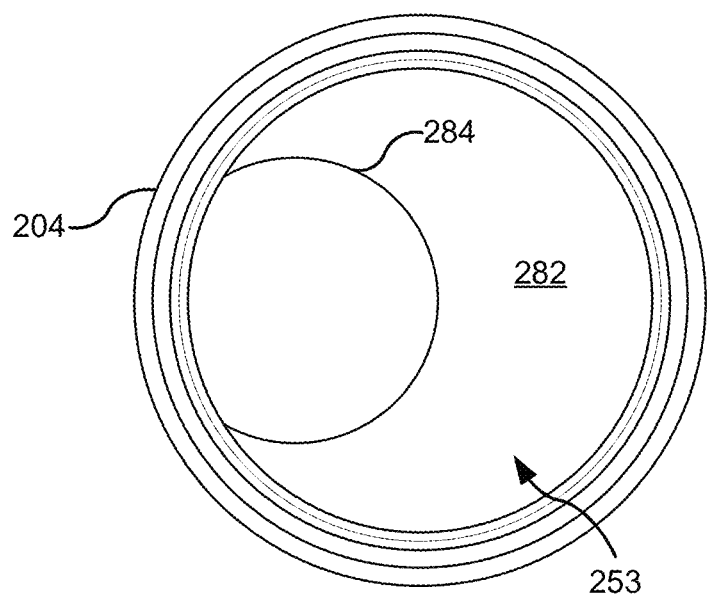
FIG. 3E shows a bottom view of the first device housing of the device of FIG. 2.

Different views of the first device housing 204 are shown in FIGS. 3A-3F, and are discussed collectively below. In particular, FIG. 3A shows a front view of the first device housing 204; FIG. 3B shows a back view of the first device housing 204; FIG. 3C shows a cross sectional view of the first device housing 204 along plane A-A' of FIG. 3B; FIG. 3D shows a top view of the first device housing 204; and FIG. 3E shows a bottom view of the first device housing 204.

The first device housing 204 further includes a window 270. The window 270 may be transparent and is used for viewing a visual output indicative of presence or absence of infectious agent in the sample. Further, the window 270 may also be used to determine a fill level of the sample during sample collection. As such, the window 270 may include a fill level indication 276 that provides an indication of an amount of sample required during testing. In some examples, different fill levels may be indicated depending on the type of sample (e.g., saliva fill level, serum fill level, pre-treated sample fill level, etc.).

While the present example shows the window 270 with beveled edges, it will be appreciated that the window 270 may be configured with other types of edges (e.g., flat, seamed, rounded, etc.) to facilitate viewing of various parameters (e.g., fill level, color change, change in turbidity, foam indication, etc.) of the contents of the collection chamber 252.

In some examples, the window 270 may include a transparent window pane. In some other examples, the window 270 may be configured as an opening on the first device housing 204. In such examples, the user may view the collection chamber 252 directly without the pane, and the collection chamber may include the fill level indication 276.

Further, the window 270 may be positioned lengthwise along the first device housing 204 and may be positioned on a side closer to the collection chamber 252 (e.g., in device embodiments where the collection chamber is positioned offset from the center of the first device housing) for improved visualization of the contents of the collection chamber and/or any visual indication. The window 270 may be positioned closer to a second chamber, where nucleic acid is captured and detected, for improved visualization of indication of presence or absence of the infectious agent. For example, the window 270 may be positioned such that a separation h2 between a bottom edge of the window 270 and a bottom edge of the first device housing 204 is less than a separation h1 between a top edge of the window and a top edge of the first device housing 204. See FIG. 3A.

Referring to the cross-sectional view in FIG. 3C, the first device housing 204 includes a primary housing 253 coupled to the one or more walls of the first device housing. An upper edge of the primary housing 253 is coupled to the first device housing along a perimeter of an inner wall of the first device housing 204 (towards the proximal end 256). Attachment junction between the primary housing 253 and the wall of the first device housing 204 is indicated by 280. Further, the primary housing 253 may share a common portion with the first device housing 240. The common portion (not shown) may include the window 270 and portions of side walls flanking the window 270 along the length of the first device housing 204. At the bottom, the primary housing 203 may be attached to an inner wall portion that is below the window 270.

Further, the primary housing 253 comprises portion 282 for housing a receiving chamber 208 for receiving the sample, and a longitudinal portion 284 for housing the collection chamber 252. The receiving chamber 208, and thus, the portion 282 of the primary housing 253, are each configured as an inverted conical frustum having a lower base and an upper base, wherein a lower base diameter is less than the upper base diameter. The lower base of the receiving chamber 208 and an upper edge of the collection chamber 252 may be coupled to form a single primary chamber. Thus, the primary chamber comprising the receiving chamber 208 and the collection chamber 252 may be positioned in the primary housing 253 such that the primary housing 253 forms a sleeve underneath the receiving chamber 208 and the collection chamber 252.

Further, towards the distal end 254 of the first device housing, the longitudinal portion 284 of the primary housing may include a scoring 264 that aligns with the scoring 262 on the collection chamber 262 to enable efficient breakage of the collection chamber when the second chamber is attached to the first device housing 204 during detection.

Further, the primary housing 253 may be positioned offset from a central longitudinal axis of the first device housing 204. That is, the primary housing 253 is positioned annularly within the cylindrical first device housing, however, a central longitudinal axis of the primary housing is offset from the central longitudinal axis of the first device housing 204. The offset is towards the window 270 such that the collection chamber 252 within the primary housing is positioned closer to the window 270, which provides improved visualization of sample as well as diagnostic readout during the detection phase. For example, during sample collection, the position of the collection chamber 252 offset from the center of the first device housing 204 and closer to the window 270 enables the user to efficiently determine (without ambiguity and/or errors) if a desired amount of sample has been collected (e.g., if the sample has been collected upto a fill line on the housing 204 and/or on the collection chamber 252). Further, when the readout is generated, the placement of the collection chamber closer to the window 270 improves visualization of the read-out generated (color change, turbidity, foam generation, etc.)

In some embodiments, there may be a separation between the inner walls of the primary housing 253 and the collection chamber 252. Within the separation, one or more heating features (e.g., chemical heating, electrical heating elements, etc.) as discussed above at FIGS. 1A and 1B may be provided for heat inactivation of proteinase enzymes and/or for achieving a temperature within an optimal range of the restriction endonuclease used in the detection of the infectious agent.

In some embodiments, the receiving chamber 208 and the collection chamber may be housed within the first device housing 204 without the primary housing 253.

Referring to FIG. 3D, it shows a top view of the first device housing 204. The receiving chamber 208 comprises a first upper opening 242 having a first diameter and a second lower opening 246 having a second diameter, wherein the second diameter is less than the first diameter.

As discussed above, the receiving chamber 208 may be configured as an inverted conical frustum, which facilitates more efficient sample collection from the subject. For example, the subject may provide saliva into the collection chamber 252 through the receiving chamber 208. Further, the lower opening 246 is offset towards the window 270 from the center of the upper opening 242, which allows the user to quickly visualize the amount of sample collected through the window and determine whether the sample has reached the fill level, which may be indicated on one or more of the first device housing 204, the window 270 and the collection chamber 252 (which is visible through the window 270).

Figure 4:
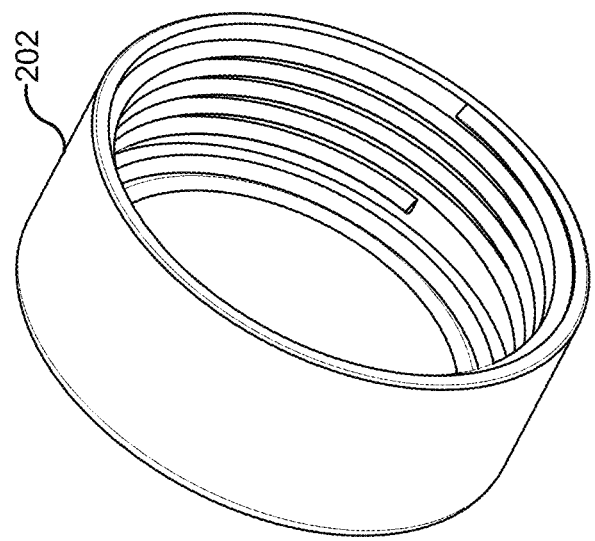
FIG. 4 shows a perspective view of a second device housing of the device of FIG. 2.
Figure 5:
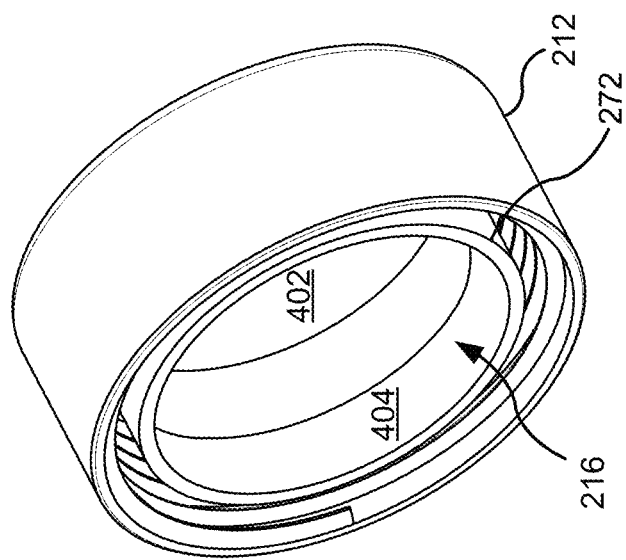
FIG. 5 shows a perspective view of a cap unit of the device of FIG. 2.

Turning to FIG. 4, it shows a perspective view of the second device housing 212 including a second chamber 216 formed by annular wall 272 and base 402. The second chamber 216 includes a nucleic acid capture portion 404 on the inner surface of the annular wall 272 and a read out generation portion 402. The nucleic acid capture portion 404 is configured to capture selective nucleic acid sequences in the genomic nucleic acid molecule of the infectious agent. Further, the second chamber 216 includes a second solution comprising a restriction endonuclease that recognizes a restriction site, which is generated upon a complementary portion of the genomic nucleic acid hybridizing with a single stranded nucleic acid molecule in the nucleic acid capture portion 402. Details of the nucleic acid capture portion 402 will be described below with respect to FIGS. 7A-7B. Further, the readout generation portion 404 is configured to generate a visual readout responsive to the nucleic acid capture portion 402 recognizing the selective nucleic acid sequences of an infectious agent in the sample and the second solution cleaving the hybridized nucleic acid molecules.

In one example, the second device housing 212 is configured as a closure unit comprising threads for coupling with the first device housing 204. Further, the second device housing 212 includes an openable seal, the openable seal configured to maintain the second solution within the second chamber 216 when the second device housing is not attached to the first device housing at the distal end. The openable seal is shown at FIG. 2 by 214. In some examples, the openable seal may be configured with a diameter greater than or equal to the annular wall 272 such that the second chamber 216 is completely sealed by the openable seal when the second device housing 212 is not coupled to the first device housing 204 at its distal end. After the sample has been treated with the first solution in the collection chamber 252 and a pre-determined duration has passed for the genomic nucleic acid of the infectious agent to be released (if present), the second device housing 212 may be screwably coupled to the first device housing 204. The screwing motion or twisting motion during coupling the second device housing 212 with the first device housing may release the openable seal as well as generate a break at the scoring 262 of the collection chamber 252 (and the primary housing 253, if present). Responsive to the second device housing 212 being coupled with the first device housing 204 at the distal end 254 and the seal(s) breaking, the combined solution containing the genomic nucleic acid of the infectious agent in the collection chamber 252 may flow into the second chamber 216, and merge with the second solution in the second chamber 216. Upon merging, the genomic nucleic acid of the infectious agent is now available for capture (via hybridization) at the nucleic acid capture portion 404 of the second chamber 216.

In some embodiments, the first device housing 204 may include more than one collection chamber 252. For example, more than one primary chamber may be included, which may be used as positive or negative controls. As a non-limiting example, a positive control chamber and/or a negative control chamber may be included within the first device housing 204 or may be configured as separate devices. Each of the positive control chamber and the negative control chamber may be coupled with a respective positive control second chamber and a respective negative control second chamber, during detection. In the positive control chamber, the corresponding collection chamber may include extracted genomic DNA that may hybridize with the nucleic acid capture portion to generate a positive control signal via the corresponding positive control detection portion. In the negative control chamber, the corresponding negative control collection chamber may not include any nucleic acid or may include other negative control genomes that may not be hybridized at the nucleic acid capture portion in the corresponding negative control second chamber. Thus, in the control chambers, sample from the subject is not provided. Further, each of the positive control readout and the negative control readout may be visualized via one or more corresponding windows. Further, in some embodiments, the one or more additional chambers may be configured as parallel chamber, positioned parallel to the collection chamber 152 that receives the sample.

In some embodiments, one or more additional test collection chambers and corresponding detection chambers may be included to detect different strains of an infectious agent (e.g. different strains of Coronavirus). In some embodiments, the one or more additional test chambers and corresponding detection chambers may be configured as separate devices, and may be included in a kit configured for detecting different strains of an infectious agent. Thus, the corresponding nucleic acid capture portions in corresponding detection chambers may be configured for detecting different strains. For example, the kit may include a first device for detecting a first strain, wherein the first device includes a first collection chamber and a first detection chamber comprising a first nucleic acid capture portion configured to capture complementary genomic nucleic acid fragment of the first strain, a second device for detecting a second strain, wherein the second device includes a second collection chamber and a second detection chamber comprising a second nucleic acid capture portion configured to capture complementary genomic nucleic acid fragment of the second strain, and so on.

Referring next to FIG. 6A, it shows a device 600, which is an example of device 100 or device 200. The device 600 is used for determining whether or not a subject is infected with an infectious agent. As discussed above with respect to device 200 and device 100, the device 600 is portable and can be easily and efficiently operated by a user who may not have technical training. As such, the device 600 may be used at home or anywhere outside clinical environment without the need for laboratory equipment or costly instrumentation. Further, the device 600 may be used at any point-of-care setting, including health care settings, home setting, field use, for diagnostic purposes.

Device 600 includes a primary chamber 606 comprising a receiving chamber 608 and a collection chamber 652. The receiving chamber 608 is coupled to the collection chamber 652 such that fluid sample from the receiving chamber flows into the collection chamber 652. In some examples, a one-way valve may be included at the junction between the receiving chamber 602 and the collection chamber 652 in order to prevent backflow of bodily fluid samples or any solution from the collection chamber flowing back into the receiving chamber 608. The primary chamber 606 is disposed within a first device housing 604. The device 600 further includes a detection chamber 616 disposed within a second device housing 612. As shown in FIG. 6A, the second device housing 612 may not be coupled to the first device housing 604 during sample collection and treatment with a first solution 610 stored in the collection chamber 652. In some examples, the second device housing 612 may be configured as a closure unit including threads for screwing on to a proximal end 656 of the first device housing 604. The second device housing 612 comprises an openable seal 614 that may be opened or ruptured when the second device housing 612 is coupled to the distal end 654 of the first device housing 604. However, the openable seal is not ruptured or opened when the second device housing is coupled to the proximal end 656 of the first device housing during storage and transportation (that is, when not in use).

During testing, a sample 601 from the subject is input into the collection chamber 652 via the receiving chamber 608. The receiving chamber 608 is configured to efficiently receive fluid samples directly from the subject (e.g., without spillage). In one example, as shown, the receiving chamber has an inverted cone shape with opening at a lower base that connects to the collection chamber 652. In this example, the sample 601 is a saliva sample comprising salivary enzymes 603 and viral particles 605 (e.g., from the subject infected with the virus that is detectable in the saliva). The subject may directly spit the saliva sample into the receiving chamber 608. The saliva sample 610 then flows into the collection chamber 652 and combines with a first solution 610 stored therein. While the present example is described with respect to viral particles, the device 600 may be configured to detect any infectious agent (e.g., bacteria, viruses, fungi, yeast, etc.). Further, the device 600 may be configured to detect a particular type and strain of virus (e.g., SARS-CoV-2) or bacteria as further discussed below.

The first solution 610 includes one or more compositions for deactivating DNase and RNase present in the sample. The one or more compositions may include an RNase inhibitor, such as DEPC, and enzymes, such as proteinase K, for example. The one or more compositions may be suspended in a buffer (e.g., water, phosphate buffered saline, PBST, Tris buffer, or the like). In some examples, the one or more compositions may be suspended in a lysis buffer. Suitable lysis buffers for various cell types are known in the art and commercially available. As but one example, a suitable lysis buffer can comprise a detergent and a buffer molecule(s). For example, an exemplary cell lysis buffer can comprise SDS (e.g., 10% SDS), Tris-HCl (e.g., at 1 M, pH 8.1), and EDTA (e.g., at 0.5 M, pH 8).

Upon combining the saliva sample with the first solution 610 in the collection chamber, and after a predetermined duration has passed, the second device housing 612 may be coupled to the distal end 654 of the first device housing. The second device housing 612 comprises a second solution and an openable seal 614. The openable seal is opened or ruptured by coupling of the second device housing 612 to the distal end 654 of the first device housing. The coupling also causes a distal portion of the collection chamber to open or rupture. As a result, the saliva and the first solution mixture from the collection chamber is flowed into the second chamber 616. At the second chamber 616, responsive to detecting the genomic nucleic acid of the infectious agent, a visual indication 660 is generated, which may be viewed or detected by a user through a viewing window 670. In this example, the visual indication 660 is foam generation. However, other indications, such as color change, turbidity change, etc., may be used. Details of the second chamber and the mechanism of detection are described below with respect to FIGS. 7A and 7B.

Figure 7B:
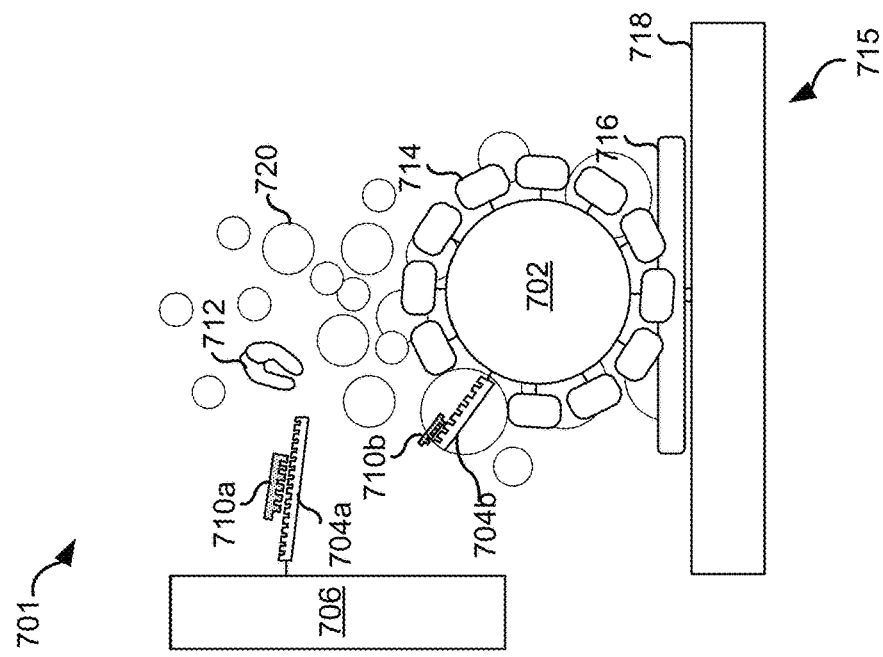
FIGS. 7A and 7B show enlarged portions of a second chamber of a device, illustrating nucleic acid capture and detection at the second chamber, for determining the presence or absence of an infectious agent in a sample, according to an embodiment of the disclosure.
Figure 7A:
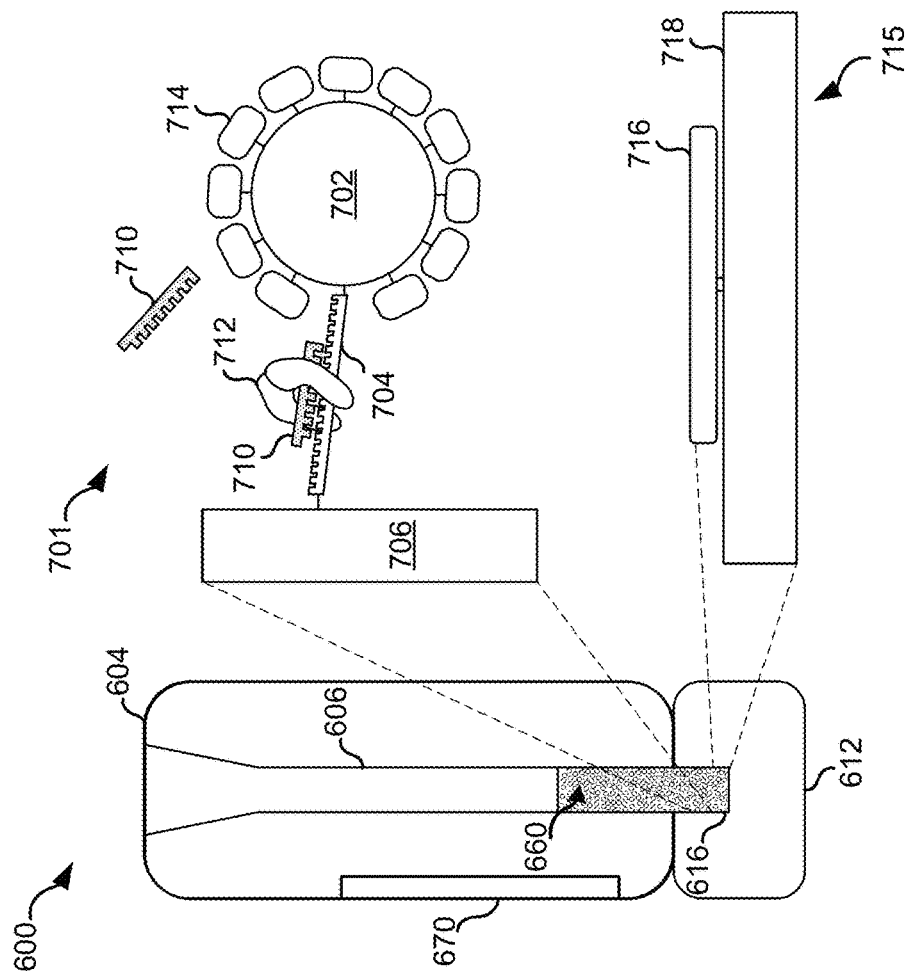

Turning next to FIGS. 7A and 7B, the figures show enlarged schematics of the second chamber 616, illustrating an example recognition of genomic nucleic acid of an infectious agent at a nucleic acid capture portion 701 (FIG. 7A) and an example read-out generation responsive to the recognition nucleic acid at a read-out portion 715 (FIG. 7B).

The second chamber 616 (alternatively referred to herein as the detection chamber) comprises the nucleic acid capture portion 701 configured to recognize and hybridize with genomic nucleic acid of the infectious agent. The nucleic acid capture portion 701 comprises a solid substrate 706. The solid substrate 706 may be a coating (e.g., silica-based coating) on the inner side walls of the second chamber 616 or the inner side walls itself may be used as the solid substrate 706. The nucleic acid capture portion 701 may be separated from the read-out portion 715. In some examples, an upper portion of the inner side walls above a level of the second solution in the second chamber 616 is configured as the nucleic acid capture portion 701. Example method for covalent attachment of single stranded DNA molecules to a surface is described in more detail by Schlingman et al., in Colloids Surf B Biointerfaces. 2011; 83(1):91-95.; which is incorporated by reference herein in its entirety. In some embodiments the ss-DNA oligomers may be attached on a scaffold surface in order to increase a surface area of the nucleic acid capture portion. For example, the scaffold surface may have extensions and/or corrugations to increase the surface area.

The scaffold surface may be resin, filter, fiber, sheet, a matrix, biocompatible and/or biodegradable scaffold material, or the like. Suitable materials for the scaffold surface include, without limitation, a synthetic polymer, biopolymer, latex, or silica. Such materials are well known in the art. Non-limiting examples of matrix structures include foams, fiber mats, 3-dimensional scaffolds, non-woven mats, woven materials, knit materials, fiber bundles, and fibers and other material formats (See, e.g., Rockwood et al. Nature Protocols 2011 6:1612-1631 and US patent Publications U.S. Pat. No. 8,172,901; each of which is incorporated by reference herein in its entirety). The structure of the matrix can be selected by one of skill in the art depending upon the intended application of the composition, e.g., electrospun matrices can have greater surface area than foams.

Further, the ss-DNA oligomers 704 may comprise 10 or more nucleotides. The ss-DNA oligomer length may range from 10 nucleotides to 500 nucleotides. The ss-DNA oligomers 704 includes a first nucleotide sequence that binds specifically to a target sequence present in the genome of the infectious agent to be detected. As a non-limiting example, the ss-DNA oligomer 704 is a nucleic acid sequence that includes a first nucleic acid sequence that is complementary and binds to a target sequence, such as a region of a genomic nucleic acid of the infectious agent. Further, the ss-DNA oligomers 704 include a second nucleic acid sequence corresponding to a cleavage site (also referred to herein as restriction site) for a restriction enzyme. The restriction enzyme recognizes the ss-DNA oligomer and viral RNA heteroduplex upon the ss-DNA oligomer hybridizing with the target sequence at the restriction site. As discussed above, the restriction enzyme is included in the second solution stored in the second chamber 616. In some examples, the ss-DNA oligomer may include more than one cleavage sequence corresponding to the restriction site. That is, the second sequence may include one or more cleavage site sequences that the restriction enzyme recognizes when the heteroduplex (ssDNA oligomer and viral RNA). The second nucleic acid sequence may be located anywhere within the first nucleic acid sequence, including the 5' or 3' ends of the first nucleic acid sequence. In some examples, as mentioned above, more than one restriction site for the restriction enzyme may be included within the ss-DNA oligomer 704.

As discussed above, each of the plurality of single stranded oligomers 704 include the first sequence complementary to the target sequence in the nucleic acid genome of the infectious agent, and the second sequence that corresponds to a restriction site of the restriction endonuclease in the second solution. In some embodiments of any of the aspects, the first sequence can have at least 90%, at least 91%, at least 92%, at least 93%, at least 94%, at least 95%, at least 96%, at least 97%, at least 98%, at least 99%, or 100% complementarity with the target sequence. In some examples, the second sequence is part of the first sequence. That is, the restriction site of the restriction endonuclease is in the first sequence. In some examples, more than one restriction site may be included. That is, the single stranded oligonucleotide may include one or more restriction sites for the restriction endonuclease. As a non-limiting examples, at least 2 restriction sites, at least 3 restriction sites, at least 4 restriction sites, at least 5 restriction sites, or at least 6 restriction sits may be included based on an overall length of the single stranded oligonucleotide 704 used in the nucleic acid capture portion.

Further, the restriction enzyme that is included in the second solution is based on the genomic nucleic acid of the infectious agent. In particular, the restriction enzyme is based on the type of genomic nucleic acid (e.g., RNA or DNA) and based on the sequence (e.g., if the target sequence that is unique to the infectious agent includes the restriction site). For example, for RNA viruses, a restriction enzyme that recognizes RNA-DNA hybrid and cleaves the RNA-DNA hybrid may be used. As a non-limiting example, restriction enzyme AvaII may be used to cleave RNA-DNA hybrid. Thus, in this example, the single stranded oligomer 704 includes a first sequence complementary to a target sequence of a portion of genomic nucleic acid of the infectious agent and further includes one or more restriction sites for AvaII. Other restriction enzymes that can be used for recognizing and cleaving DNA-RNA heteroduplexes include, but not limited to, the following: AvaII, AvrII, BanI, HaeIII, HinfI and TaqI.

In some examples, if the infectious agent has a DNA genome, then a restriction enzyme that cleaves DNA-DNA duplex may be used, and depending on the availability of the corresponding cleavage site (that is, restriction site) within the target sequence of the genome of the infectious agent.

As discussed above, one end (e.g., 3' end) of the ss-DNA oligomer 704 is attached to the solid substrate 706 (or a scaffold with greater surface area, for example). The other end (5'end) is covalently coupled to a protein tag (e.g., biotin) which may covalently couple to an interacting protein (e.g., streptavidin) coated onto bead(s) 702. In some examples, a linker may be attached to the 5' end and/or the 3' end of the ss-DNA oligomer 704 to increase oligomer flexibility, reduce steric hinderance, and improve availability of the oligomer 704 for hybridizing with the complementary nucleic acid sequence present in the genomic nucleic acid of the infectious agent. The linker may be a peptide linker or a chemical modification or a combination thereof.

Further, in addition to modifications to 5' end and/or 3' end for substrate attachment and/or bead attachment, the ss-DNA oligomer 706 may include one or more modified bases, for example, to reduce self-dimerization or secondary structure formation (e.g., hair-pin loops). An example modified base is 2'-methoxyethoxy cytosine.

Beads 702 may be solid particles conjugated with small protein molecules. Example beads 702 that may be used include but not limited to streptavidin coated beads, avidin coated beads, protein G coated beads, protein A conjugated beads, anti-biotin beads, or the like. Further, the beads 702 may be magnetic beads, silica beads, silica-like beads, or agarose beads.

Further, a reporting label 714 is conjugated to the beads 702. The reporter label 714 may be a tagged enzyme including a tag that is conjugated with the small protein molecule on the beads. Example tags include, but not limited to biotin (for streptavidin beads), or protein A or protein G (for protein G or protein A coated beads respectively). As used herein, the term "conjugated" refers to the attachment of at least two entities to form one entity. The joining of the two entities can be direct (e.g., via covalent or non-covalent bonds) or indirect (e.g., via linkers etc.). Thus, conjugation can be by means of linkers, chemical modification, peptide linkers, chemical linkers, covalent or non-covalent bonds, or protein fusion or by any means known to one skilled in the art, e.g., click chemistry or biorthogonal chemistries as described in Devaraj. ACS Central Science 2018 4:952-9; which is incorporated by reference herein in its entirety. The joining or conjugation can be permanent or reversible.

The reporting label 714 is an enzyme that generates a visually detectable product upon interaction with its corresponding substrate. For example, when exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase, 4-Nitrophenyl β-D-glucopyranoside, and acetylcholinesterase. In still other examples, the reporting label may be gold nanoparticles conjugated to glycol chitosan as described at Kim K et al. at "Highly Sensitive Colorimetric Assay for Determining Fe3+ Based on Gold Nanoparticles Conjugated with Glycol Chitosan. J Anal Methods Chem." 2017, which is incorporated by reference in its entirety.

Taken together, the nucleic acid capture portion 701 includes a plurality of ss-DNA oligomers 704. Each of the plurality of ss-DNA oligomers 704 is conjugated to a solid substrate 706 on one end and conjugated to the bead 702 on another end, wherein the bead 702 is conjugated with the reporting label 714, which when exposed to its substrate generates a visually detectable signal.

The substrate corresponding to the reporting label 714 is embedded within a polymeric disk 716 coupled on to a bottom surface 718 of the second chamber 616. When the target nucleic acid sequence of the infectious agent is not present in the sample and solution mixture flowing from the collection chamber 652, the beads 702 with the reporting label 714 remain attached to the solid substrate 706 via the ss-DNA oligomer 704. Thus, the reporting label 714 is not exposed to the substrate and visual output is not generated (that is, no detectable color change or visible foam or change in turbidity), which indicates absence of the infectious agent.

When the ss-DNA oligomer 704 recognizes and hybridizes with a target fragment 710 of the infectious agent, a selected restriction enzyme 712 recognizes the ss-DNA 704 and target fragment 710 hybrid (that is DNA-RNA heteroduplex in this example) at the restriction site. The restriction enzyme 712 is provided in a second solution in the second chamber 616. The second solution may further comprise proteinase inhibitors for deactivating proteinase in the first solution and sample mixture (flowing from the collection chamber 652). The restriction enzyme 712 and the proteinase inhibitors may be suspended in a reaction buffer. Non-limiting examples of reaction buffers that can be used include the M-type universal buffer recipe. See, e.g., Takara Bio (Relative Activity of Restriction Enzymes in Universal and Basal Buffers, 2020) which is optimal for the restriction enzyme AvaII. The recipe for a 1× solution is as follows: 10 mM Tris-HCl (pH 7.5), 10 mM MgCl2, 1 mM dithiothreitol, 50 mM NaCl. This buffer and variations thereof can be used as long as they support enzyme activity (e.g., reporting label 714 activity (e.g., catalase, β-galactosidase activity) and proteinase K inhibitor activity).

Upon formation of the restriction site by hybridization (when infectious agent is present), the restriction enzyme 712 recognizes the restriction site and cleaves the ss-DNA oligomer 704 and target nucleic acid fragment 710 hybrid at the restriction site, which releases the beads 702 from the substrate 706. FIG. 7B shows example cleavage of the ss-DNA oligomer 704 and target nucleic acid fragment 710 hybrid. The beads 702 when released fall onto the polymeric disk 716 comprising the substrate for the label 714 conjugated to the beads, thereby generating a read-out which can be visually detected.

For example, catalase may be used as a label coating the beads, and the catalase enzymes substrate, hydrogen peroxide, may be embedded in the polymeric disk. Responsive to the ss-DNA oligomer 704 hybridizing with the target nucleic acid fragment 710, and cleavage by restriction enzyme 712, the beads with the catalase coating may be released from the substrate 706 and may travel to the polymeric disk including the catalase substrate, hydrogen peroxide. Upon the beads interacting with the polymeric disk, foam bubbles 720 are generated, which can be easily visualized via window 670.

As an example, after the expiration of a set period of time (e.g., 10 minutes), the visible signals are observed and/or detected (e.g, as viewed through window 670 in the first device housing 604). Observation and/or detected can be done by the human eye. For example, the device can be provided with a key or instructions that provide the user with the information necessary to interpret results, e.g., as in the case of home pregnancy test kits. In such embodiments, the possible results and number of visualization areas can be minimal to avoid confusion or incorrect interpretation by lay users, e.g, the device can be designed to detect a single target or target class, such that a result is categorized as "yes" or "no." Observation and/or detection by the human eye can also be performed by a medical professional. In such cases, the device can be provided with a key or instructions that provide the medical professional with the information necessary to interpret results. In such embodiments, the possible results and number of visualization areas can be complex enough to provide multiple possible outputs, e.g, the device can be designed to detect multiple targets or target classes (e.g., a multiplexed device). Particularly when the device is configured for evaluation by a computer or medical professional, the information can be interpreted beyond a binary "yes" or "no", as the amount of targets may be informative and diagnostic (e.g., severity of infection).

Observation and/or detection can also be performed with a device which can discern the signals. For example, a photograph of the visual indication can be taken (e.g, as viewed through viewing windows 670) using a smartphone, tablet, digital camera, or the like. The captured image can then be analysed by a computer program and/or medical professional in order to interpret the results based on color, intensity of the color, etc.

In this way, visual signals are generated that enable quick and accurate detection of the presence of a target infectious agent without nucleic acid amplification and expensive instrumentation.

To rapidly detect target viral RNAs, the ability of the restriction enzyme AvaII can be leveraged to cleave DNA/RNA heteroduplexes at AvaII specific restriction sites. Other restriction enzymes that can be used include, but not limited to, the following: AvaII, AvrII, BanI, HaeIII, HinfI and TaqI.

In one embodiment, a device for assessing presence or absence of an infectious agent in a bodily fluid sample, comprises: a detection chamber disposed in a housing, the detection chamber comprising a first nucleic acid capture portion and a second readout generation portion. In a first example, the device further comprises a second solution, the second solution including a restriction endonuclease. In a second example of the device, which optionally includes the first example, the nucleic acid capture portion comprises a first substrate coupled to a plurality of enzyme coated beads via a plurality of single stranded oligonucleotides, wherein each of the plurality of single stranded oligonucleotides comprises a first sequence complimentary to a target sequence in the genomic nucleic acid of the infectious agent and comprises one or more second sequences corresponding to a restriction site of the restriction endonuclease. In a third example of the device, which optionally includes the first and/or the second examples, the second readout generation portion comprises a substrate of an enzyme coating the enzyme coated beads. In a fourth example of the device, which optionally includes one or more of the first through third examples, the substrate is embedded in a polymeric mesh coupled to the inner bottom surface. In a fifth example of the device, which optionally includes one or more of the first through fourth examples, the second solution further includes one or more proteinase inhibitors. In a sixth example of the device, which optionally includes one or more of the first through fifth examples, the device further comprises a transparent or translucent window configured for viewing a visible indication generated by the second readout generation portion. In a seventh example of the device, which optionally includes one or more of the first through sixth examples, the nucleic acid capture portion is positioned on an inner wall or a portion thereof of the detection chamber and the readout generation portion is position on an inner bottom surface or a portion thereof of the detection chamber. In an eighth example of the device, which optionally includes one or more of the first through seventh examples, the detection chamber includes an openable seal. In a ninth example of the device, which optionally includes one or more of the first through eighth examples, the detection chamber is configured to couple to a primary chamber disposed in another housing, and when coupled, the detection chamber is configured to receive a solution mixture including the bodily fluid sample via the primary chamber. In a tenth example of the device, which optionally includes one or more of the first through ninth examples, the solution mixture further includes one or more proteinase and DEPC to inactivate DNase and RNase in the bodily fluid sample.

In one embodiment, a composition for detecting an infectious agent in a biological fluid sample, the composition comprising:

(a) a single stranded oligonucleotide comprising a first nucleotide sequence complementary to a portion of genomic nucleic acid sequence of the infectious agent or a fragment thereof and at least one second nucleotide sequence corresponding to a restriction site of a restriction enzyme;

(b) a first solid support, wherein the first solid support is conjugated to the single stranded oligonucleotide at one end of the single stranded oligonucleotide; and (c) an enzyme conjugated bead, the enzyme conjugated bead conjugated to the single stranded oligonucleotide at another end of the single stranded oligonucleotide.

In a first example of the composition, the single stranded oligonucleotide is a single stranded deoxyribonucleic acid oligonucleotide.

In a second example of the composition, which optionally includes the first example, a length of the single stranded oligonucleotide is in a range between 10 base pairs and 500 base pairs.

In a third example of the composition, which optionally includes any of the first or the second examples, each of the enzyme conjugated beads comprise a plurality of enzyme polypeptides conjugated to a bead.

In a fourth example of the composition, which optionally includes one or more of the first to third examples, the plurality of enzyme polypeptides are selected from the group consisting of horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase.

In a fifth example of the composition, which optionally includes one or more of the first to fourth examples, the restriction enzyme is selected from the group consisting of: AvaII, AvrII, BanI, HaeIII, HinfI, and TaqI.

In a sixth example of the composition, which optionally includes one or more of the fifth examples, the infectious agent is selected from the group consisting of viruses, bacteria, yeast, fungi, and archaea.

In a seventh example of the composition, which optionally includes one or more of the first to sixth examples, the infectious agent is a coronavirus and the single stranded oligonucleotide has a sequence selected from the group consisting of SEQ ID NO: 2-16.

In one embodiment, a method for a nucleotide capture portion comprises coating a solid substrate with a plurality of single stranded oligonucleotides, and adding a plurality of enzyme coated beads to the solid substrate coated with the plurality of single stranded oligonucleotides to couple each enzyme coated beads to the solid substrate via one or more single stranded oligonucleotide. As a non-limiting example, biotin-tagged enzyme may be conjugated to streptavidin coated beads at less than maximum capacity (e.g., in a range between 30%-90% of maximum capacity). Thus, the remaining streptavidin on the streptavidin coated beads (that are not bound to biotin tagged enzyme) are available for binding to single stranded oligonucleotide (e.g., ss-DNA oligomer). When the enzyme coated beads (with remaining streptavidin) are added to the solid substrate coated with single stranded oligonucleotide, the beads conjugate to a second biotin tag coupled to 5' end of the single stranded oligonucleotide while the 3' end of the single stranded oligonucleotide remain bound to the solid substrate (e.g., walls of the second chamber).

FIGS. 8A-8D show another example of a device 800 for detecting the presence of an infectious agent. The device 800 is similar to device 600, device 200, and device 100 described herein. The device 800 includes a primary chamber 806 for neutralizing the enzymes in the sample and releasing the target nucleic acid (e.g., viral nucleic acid) from the pathogenic cells or particles. The device 800 further includes a detection chamber 816 comprising a viral nucleic acid capture portion 860, the viral nucleic acid capture portion comprising ss-DNA oligomers conjugated to enzymatic label coated particles (or enzymatic label coated beads). The enzymatic label coated beads may be attached to walls of the detection chamber 816 via the ss-DNA oligomers that are complementary to and specific to a target virus. The present example is described with respect to a single stranded RNA virus, however, it will be appreciated that the devices, composition, and methods described herein can be employed to detect any infectious agent that may be found in a bodily fluid sample without departing from the scope of the disclosure. Further, the device includes a polymeric mesh 818 comprising a substrate, the substrate corresponding to the enzymatic label on the beads of the nucleic acid capture portion 860. The polymeric mesh 818 is positioned downstream of the nucleic acid capture portion 860, downstream in a direction of flow of sample from the primary chamber 806 to the second chamber 816.

Further, at a junction between the primary chamber 806 and the second chamber 816, a valve 814 (plastic gate valve) operated via an actuator 815 is provided to control release and flow of sample from the primary chamber to the second chamber 816.

When viral RNA is introduced to the device 800 via a saliva sample, it hybridizes to the ssDNA strands that secure the enzymatic label (e.g., β-galactosidase) decorated beads to a solid substrate (e.g., a portion of the walls of the second chamber). The hybridization results in restriction enzyme-mediated cleavage of the resulting DNA/RNA heteroduplexes, releasing the β-galactosidase decorated beads into the solution, which leads to visible color change, indicating a positive test result (FIG. 8D). If there are no viral RNAs present in the saliva sample, the beads will remain linked to the solid substrate, which generates to a negative test result (FIG. 8C) The primary chamber 806 comprises proteinase K and DEPC to inactivate salivary DNases and RNases while the second chamber 816 comprises beads linked to a solid substrate via a ssDNA oligonucleotide, the restriction enzyme (e.g., AvaII), an irreversible proteinase K inhibitor, and the immobilized substrate (e.g., Red-Gal for β-galactosidase).

In order to perform the test, a user may input a fluid sample into the primary chamber 806 via a sample entry port 806. The user may then wait for a threshold duration (e.g., 10 minutes) in order to allow the proteinase K to digest salivary nucleases and the DEPC to further inactivate any remaining RNases. Next, after the threshold duration has passed, the user may actuate a button which opens the valve 814, allowing the contents of the primary chamber 806 to enter the second chamber 806. At the second chamber 806, the irreversible proteinase K inhibitor inactivate the proteinase K. If target viral RNA is present, the beads undergo AvaII-mediated release. As shown at FIG. 8D by broken arrows, the beads travel to the polymeric mesh 818 and responsive to the enzymatic label on the beads being exposed to the substrate immobilized in the polymeric mesh 818, a visual indication 820 (e.g., red color) appears on the polymeric mesh 818, which may be visualized via a window within the second chamber 816 (e.g., at opposite wall of the second chamber), indicating a positive test result. If target viral RNA is not present, the beads will remain linked to the solid substrate, preventing color from forming, which indicates absence of the virus in the sample and therefore, indicates a negative test result (FIG. 8C).

Figure 9:
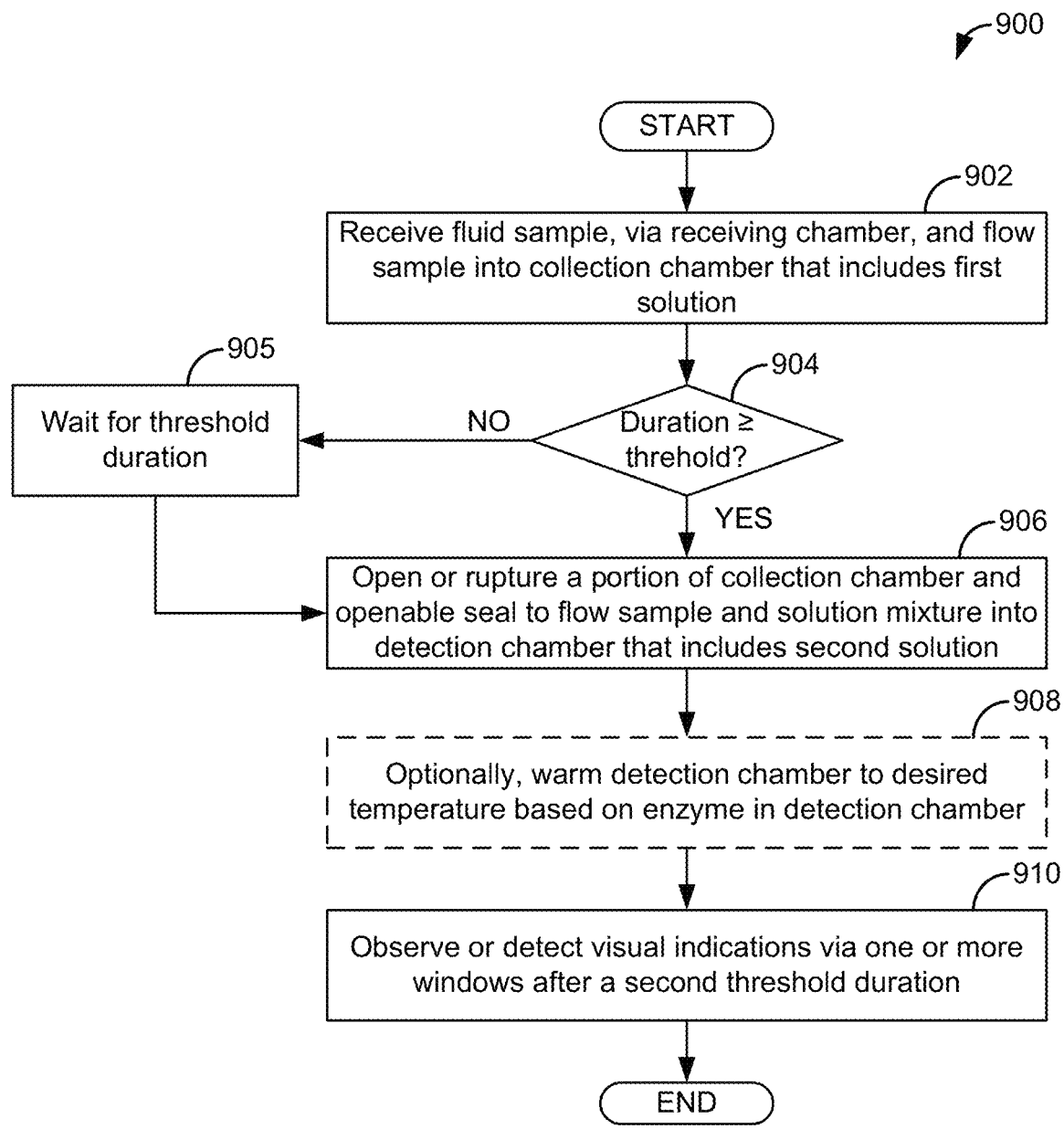
FIG. 9 shows a high level flow chart of an example method for detecting the presence or absence of an infectious agent, according to an embodiment of the disclosure.

Referring now to FIG. 9, it shows a high-level flow chart of an example method 900 for detecting presence of an infectious agent in a bodily fluid sample, according to an embodiment of the disclosure. Wherein the infectious agent is detectable in the bodily fluid sample. Further, the method 900 may be used for detecting the presence of any infectious agent in the bodily sample, including, bacteria, archaea, fungi, yeast and/or viruses. The method 900 may be performed using a device, such as device 100, 200, 600, 700, or 800 described herein. The method 900 will be described herein with respect to device 600 described at FIGS. 6A, 6B, 7A, and 7B; however, it will be appreciated that the method 900 may be adapted for use with similar devices without departing from the scope of the disclosure.

At 902, the method 900 includes receiving a bodily fluid sample from a subject into a primary chamber, such as primary chamber 606. For example, the bodily fluid sample (e.g., saliva) may be received via a receiving chamber, such as receiving chamber 608, and flowed into the collection chamber, such as collection chamber 652. When collecting the sample, a secondary chamber, such as secondary chamber 616, may be separated from primary chamber. That is, the primary chamber and the secondary chamber may be separated so as to not mix the contents of the primary chamber and the secondary chamber until detection phase.

At 904, the method 900 includes determining if a threshold duration has passed after transferring the fluid sample into the collection chamber. The collection chamber comprises a first solution which includes a proteinase enzyme to deactivate DNases and RNases present in the sample. Further, the first solution may include DEPC to ensure deactivation of RNases. Furthermore, the first solution may include a buffer that facilitates lysis of infectious agents in the sample and release of the genomic nucleic acid of the infectious agents, thereby making the genomic nucleic acid or fragments of the genomic nucleic acid available for capture during subsequent steps.

Accordingly, upon transferring the sample to the collection chamber, a user may wait for the threshold duration, where the threshold duration is based on a duration required for neutralizing the DNAse and RNase enzymes in the sample, and ensure lysis of the cells or particles of the infectious agent. Thus, the threshold duration may be based on the type of infectious agent detected (e.g., bacteria, virus, etc).

If the answer at 904 is YES, the method 900 proceed to 906. Otherwise, the user may wait until the threshold duration has passed and then proceed to 906. At 906, the method 900 includes opening or rupturing one or more of an openable seal sealing the second chamber and a distal portion of the collection chamber along a score line towards the closed end of the collection chamber. The opening or rupturing may be performed by screwing or twisting the second chamber onto the distal end of the first housing that includes the primary chamber. By opening or rupturing the openable seal and opening or rupturing at least a portion of the distal end of the collection chamber, the contents from the collection chamber may mix with the contents from the second chamber. Further, upon opening or rupturing, the genomic nucleic acid is exposed to the complementary single stranded DNA attached to the inner walls of the second chamber.

Next, at 908, optionally, the device may be heated (e.g., via chemical based heating or via one or more electrical heating elements coupled to the device) to a desired temperature that is within an optimum range for the restriction endonuclease.

Next, at 910, the method 900 includes observing visual indications showing presence of the infectious agent via one or more viewing windows. In one example, when the beads are coated with catalase and hydrogen peroxide is used as a substrate embedded in the polymeric mesh, upon recognition of the target genomic nucleic acid fragments by the single stranded oligonucleotide (coupled to the walls of the secondary chamber) and restriction of the genomic nucleic acid and the single stranded oligonucleotide by the restriction enzyme in the second chamber, the enzyme coated beads are released from the walls of the second chamber and travel to the substrate. Upon exposure of the enzyme coated on the beads to the substrate, a visual indication is generated (e.g., foam, color change etc). The visual indication that may confirm the presence of the infectious agent may be viewed via one or more windows. Further, as discussed above, the position of the windows may facilitate easy and clear viewing of the visual indications generated by merging of the solution from the primary chamber and the secondary chamber.

The second threshold duration may be based on a duration required by the restriction enzyme to cleave the hybridized molecules, and may vary based on the restriction enzyme used. In some embodiments of any of the aspects, the second threshold duration is at least 5 minutes. In some embodiments of any of the aspects, the second threshold duration is at least 10 minutes. In some embodiments of any of the aspects, the second threshold is at least 20 minutes. In some embodiments of any of the aspects, the second threshold duration is at least 30 minutes.

In some embodiments of any of the aspects, a total duration from sample collection to detection of visible signals is at least 10 minutes. In some embodiments of any of the aspects, the total duration is in a range between 10 and 60 minutes.

In some embodiments, after the first threshold duration, alternatively, the second solution may be added into collection chamber (separately, via the receiving chamber) and then, the collection chamber and the openable seal may be opened or ruptured to flow sample and solutions mixture into detection chamber.

In some embodiments, an intermediate chamber between the primary chamber and the secondary chamber may be present that includes proteinase inhibitors but not the restriction endonuclease. Thus, the proteinase inhibitor may neutralize the proteinase present in the collection chamber prior to passing through the secondary chamber that includes the nucleic acid capture portion and the read-out generation portion.

In some examples, the primary chamber and the secondary chamber may be separated by a first openable seal and a second openable seal. That is, the closed end of the collection chamber may be configured as the first openable seal. Thus, during detection phase, both the openable seals may be ruptured or opened simultaneously to mix the contents in both the primary and the secondary chambers.

In some embodiments multiple variants of a virus type may be detected. As a non-limiting example, multiple primary chamber and multiple secondary chambers may be used, each configured to detect a different strain of virus. In particular, the single stranded oligonucleotide in each secondary chamber may be configured to detect a different strain of a virus type.

In some embodiments of any of the aspects, the single stranded oligonucleotide comprises a recognition sequence. As an example, the recognition sequence can be a nucleic acid sequence that is complementary to a target sequence, e.g., a region of a chromosome. Accordingly, the recognition sequence will vary depending on the identity of the desired target. It is well within the skill of the art to design a recognition sequence that will specifically hybridize to any given target under specific conditions, e.g., using software widely and freely available for this purpose (e.g., Primer3 or PrimerBank, which are both available on the world wide web). In some embodiments of any of the aspects, the recognition sequence can have at least 90%, at least 91%, at least 92%, at least 93%, at least 94%, at least 95%, at least 96%, at least 97%, at least 98%, at least 99%, or 100% identity with a portion of the target sequence. In some embodiments of any of the aspects, multiple recognition sequences can be found on the same or different single stranded oligonucleotides can specifically bind to a single target sequence. As a non-limiting example, at least 2 recognition sequences, at least 3 recognition sequences, at least 4 recognition sequences, at least 5 recognition sequences, at least 10 recognition sequences, at least 20 recognition sequences, at least 30 recognition sequences, at least 40 recognition sequences, or at least 50 recognition sequences an specifically bind to a target sequence.

As used herein, the term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the Tm for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, Molecular Cloning A Laboratory Manual, 2nd Ed. Cold Spring Harbor Press (1989) and Anderson Nucleic Acid Hybridization, 1st Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

As used herein, the term "oligonucleotide" is intended to include, but is not limited to, a single-stranded DNA or RNA molecule, typically prepared by synthetic means. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array. In addition to the 100% complementary form of double-stranded oligonucleotides, the term "double-stranded" as used herein is also meant to include those form which include such structural features as bulges and loops (see Stryer, Biochemistry, Third Ed. (1988), incorporated herein by reference in its entirety for all purposes). As used herein, the term "polynucleotide" is intended to include, but is not limited to, two or more oligonucleotides joined together (e.g., by hybridization, ligation, polymerization and the like).

In some embodiments of any of the aspects, the nucleic acid e.g., a single stranded oligonucleotide linker is chemically modified to enhance stability or other beneficial characteristics (e.g., reduction of secondary structure formation). The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of nucleic acid compounds useful in the embodiments described herein include, but are not limited to nucleic acids containing modified backbones or no natural internucleoside linkages. nucleic acids having modified backbones include, among others, those that do not have a phosphorus atom in the backbone. For the purposes of this specification, and as sometimes referenced in the art, modified nucleic acids that do not have a phosphorus atom in their internucleoside backbone can also be considered to be oligonucleosides. In some embodiments of any of the aspects, the modified nucleic acid will have a phosphorus atom in its internucleoside backbone.

Modified nucleic acid backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified nucleic acid backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2- [known as a methylene (methylimino) or MMI backbone], —CH2-O—N(CH3)-CH2-, —CH2-N(CH3)-N(CH3)—CH2- and —N(CH3)-CH2-CH2- [wherein the native phosphodiester backbone is represented as —O—P—O—CH2-].

Modified nucleic acids can also contain one or more substituted sugar moieties. The nucleic acids described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO] mCH3, O(CH2).nOCH3, O(CH2)nNH2, O(CH2) nCH3, O(CH2)nONH2, and O(CH2)nON[(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties a nucleic acid, or a group for improving the pharmacodynamic properties of a nucleic acid, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the nucleic acid, particularly the 3' position of the sugar on the 3' terminal nucleotide or in 2'-5' linked dsRNAs and the 5' position of 5' terminal nucleotide. Nucleic acids may also have sugar mimetics such as cyclobutyl moieties in place of the pentofuranosyl sugar.

A nucleic acid can also include nucleobase (often referred to in the art simply as "base") modifications or substitutions.

As used herein, "unmodified" or "natural" nucleobases include the purine bases adenine (A) and guanine (G), and the pyrimidine bases thymine (T), cytosine (C) and uracil (U). Modified nucleobases can include their synthetic and natural nucleobases including but not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications. In some embodiments of any of the aspects, modified nucleobases can include d5SICS and dNAM, which are a non-limiting example of unnatural nucleobases that can be used separately or together as base pairs (see e.g., Leconte et. al. J. Am. Chem. Soc. 2008, 130, 7, 2336-2343; Malyshev et. al. PNAS. 2012. 109 (30) 12005-12010). In some embodiments of any of the aspects, oligonucleotide tags (e.g., Oligopaint) comprise any modified nucleobases known in the art, i.e., any nucleobase that is modified from an unmodified and/or natural nucleobase.

The preparation of the modified nucleic acids, backbones, and nucleobases described above are well known in the art.

The term "sample" as used herein denotes a sample taken or isolated from a biological organism, e.g., a blood, stool, mucus, or plasma sample from a subject. In some embodiments of any of the aspects, the present invention encompasses several examples of a biological sample. In some embodiments of any of the aspects, the biological sample is cells, or tissue, or peripheral blood, bodily fluid, or bodily wastes, secretions, or excretions. Exemplary biological samples include, but are not limited to, saliva, biofluid sample; blood; serum; plasma; urine; feces; sperm; mucus; tissue biopsy; organ biopsy; synovial fluid; bile fluid; cerebrospinal fluid; mucosal secretion; effusion; sweat, etc. The term also includes a mixture of the above-mentioned samples. The term "sample" also includes untreated or pretreated (or pre-processed) biological samples. In some embodiments of any of the aspects, a test sample can comprise cells from a subject. In some embodiments of any of the aspects, a test sample can comprise microorganisms from a subject.

The test sample can be obtained by removing a sample from a subject, but can also be accomplished by using a previously isolated sample (e.g. isolated at a prior timepoint and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen saliva. The frozen sample can be thawed before employing methods, assays and systems described herein. After thawing, a frozen sample can be centrifuged before being subjected to methods, assays and systems described herein. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing.

In some embodiments of any of the aspects, the methods, described herein can further comprise a step of obtaining or having obtained a test sample from a subject. In some embodiments of any of the aspects, the subject can be a human subject.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. A subject can be male or female.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "fragment", as used herein, refers to a polypeptide or a polynucleotide having a sequence length of 1 to n−1, relative to a full-length polypeptide or polynucleotide (length is n). The length of the fragment can be appropriately changed according to the purpose thereof. Examples of a lower limit of the length thereof, in the case of a polypeptide, include 3, 4, 5, 6, 7, 8, 9, 10, 15, 20, 25, 30, 40, 50 and more amino acids, and a length represented by an integer which is not specifically listed herein (e.g. 11) can also be proper as a lower limit. In addition, in the case of a polynucleotide, examples of a lower limit of the length thereof include 5, 6, 7, 8, 9, 10, 15, 20, 25, 30, 40, 50, 75, 100, 200, 300, 400, 500, 600, 700, 800, 900, 1000 and more nucleotides, and a length represented by an integer which is not specifically listed herein (e.g., 11) can also be proper as a lower limit.

In some embodiments, the methods and devices described herein relate to measuring, detecting, or determining the presence/level of at least one marker or target. As used herein, the term "detecting" or "measuring" refers to observing a signal from, e.g. a probe, label, or target molecule to indicate the presence of an analyte in a sample. In some embodiments of any of the aspects, measuring can be a quantitative observation.

As used herein, "contacting" refers to any suitable means for delivering, or exposing, the device with a sample. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Embodiments

Embodiment 1. A device for detecting an infectious agent in a sample, the device comprising:

a first device housing including a first chamber, the first chamber including a first solution for releasing a nucleic acid of the infectious agent;

a second device housing including a second chamber, the second chamber including a nucleic acid capture portion, a readout generation portion, and a second solution including at least one restriction endonuclease enzyme;

wherein the nucleic acid capture portion includes a plurality of enzyme conjugated beads, each enzyme conjugated bead attached to the second chamber via a single stranded oligonucleotide; and wherein the single stranded oligonucleotide includes a first sequence corresponding to a restriction site of the at least one restriction enzyme and a second sequence complementary to a fragment of a genomic nucleic acid of the infectious agent.

Embodiment 2. The device of embodiment 1, wherein an inner side wall of the second chamber comprises the nucleic acid capture portion; and wherein an inner bottom surface of the second chamber comprises the readout generation portion.

Embodiment 3. The device of any of embodiments 1-2, wherein the restriction endonuclease recognizes and cleaves a ribonucleic acid and a deoxyribonucleic acid hybrid molecule at the restriction site.

Embodiment 4. The device of any of embodiments 1-3, wherein the restriction endonuclease is selected from the group consisting of AvaII, AvrII, BanI, HaeIII, HinfI, and TaqI.

Embodiment 5. The device of any of embodiments 1-4, wherein the second chamber includes an openable seal, the openable seal configured to allow contents from the first chamber and contents from the second chamber to mix when opened or ruptured.

Embodiment 6. The device of any of embodiments 1-5, wherein the readout generation portion comprises a substrate of an enzyme coating the enzyme coated beads; and wherein the substrate is embedded in a polymeric mesh coupled to the inner bottom surface.

Embodiment 7. The device of any of embodiments 1-6, wherein one or more of the first device housing and the second device housing comprises one or more viewing windows for viewing a visual indication generated in the second chamber.

Embodiment 8. The device of any of embodiments 1-7, wherein the first solution comprises a proteinase enzyme; and wherein the second solution further comprises a proteinase inhibitor.

Embodiment 9. The device of claim any of embodiments 1-8, wherein the first chamber includes a sample receiving chamber coupled to a collection chamber such that the sample flows from the receiving chamber to the collection chamber; and wherein the sample receiving portion has a funnel shape or an inverted conical frustum shape.

Embodiment 10. The device of claim any of embodiments 1-9, wherein the second housing is configured as a closure unit comprising threads for coupling with the first housing.

Embodiment 11. The device of claim any of embodiments 1-10, wherein the collection chamber comprises a breakable score towards a closed end of the collection chamber.

Embodiment 12. A device for detecting an infectious agent in a fluid sample, the device comprising:
  a first chamber including a sample receiving chamber and a collection chamber, the collection chamber including a first solution;
  a second chamber including a nucleic acid capture portion and a second solution, the second solution comprising a restriction endonuclease; and
  one or more openable seals between the first chamber and the second chamber, the one or more openable seals separating the first chamber and the second chamber when sealed, and the one or more openable seals configured to allow contents from the first chamber and contents from the second chamber to mix when opened or ruptured;
  wherein the nucleic acid capture portion comprises a plurality of single stranded oligonucleotides, each of the plurality of single stranded oligonucleotides comprising:
    a first sequence complementary to a target sequence in a genomic nucleic acid of the infectious agent and including one or more restriction sites for the restriction endonuclease.

Embodiment 13. The device of embodiment 12, wherein the first chamber and the second chamber are disposed in a single housing; or wherein the first chamber is disposed in a first device housing and the second chamber is disposed a second device housing, the second device housing configured as a closure unit for the first device housing.

Embodiment 14. The device of any of embodiments 12-13, wherein the receiving chamber has an inverted conical frustum shape with a first base diameter greater than a second base diameter, and wherein a center of the second base is offset from a center of the first base.

Embodiment 15. The device of any of embodiments 12-14, wherein a central longitudinal axis parallel to a length of the collection chamber is offset from the center of the first base of the receiving chamber and aligns with the center of the second base of the receiving chamber.

Embodiment 16. The device of any of embodiments 12-15, wherein the second chamber further includes a readout generation portion on an inner bottom surface of the second chamber, the readout generation portion comprising a substrate of an enzyme coating the enzyme coated beads; and wherein the substrate is embedded in a polymeric mesh coupled to the inner bottom surface.

Embodiment 17. The device of any of embodiments 12-16, further comprising at least one window in the first device housing for viewing a visual indication generated by the readout generation portion.

Embodiment 18. The device of any of embodiments 12-17, wherein the visual indication is a colorimetric change or a turbidimetric change, or a combination thereof.

Embodiment 19. The device of any of embodiments 12-18, wherein the fluid sample is a bodily fluid of a subject and wherein the infectious agent is selected from the group consisting of viruses, bacteria, archaea, fungi, and yeast.

Embodiment 20. The device of any of embodiments 12-19, wherein the infectious agent is selected from a group consisting of a virus, an RNA virus, and a coronavirus.

Embodiment 21. The device of any of embodiments 12-20, wherein the restriction endonuclease is selected from the group consisting of AvaII, AvrII, BanI, HaeIII, HinfI, and TaqI.

Embodiment 22. A method for detecting an infectious agent in a bodily fluid sample, the method comprising:
  combining the bodily fluid sample with a first solution in a collection chamber of a device, the device comprising:
    a first chamber including a receiving chamber and the collection chamber, wherein the collection chamber comprises an openable closed end;
    a second chamber including a nucleic acid capture portion, a readout generation portion, and a second solution, the second solution comprising a restriction endonuclease, wherein the second chamber is sealed by an openable seal; and
  opening or rupturing the openable closed end and the openable seal to allow contents in the first chamber to mix with the contents in the second chamber;
  wherein the nucleic acid capture portion comprises a plurality of enzyme coated beads, each of the enzyme coated beads coupled to inner side walls of the second chamber via at least one single stranded oligonucleotide comprising:
    a first sequence complementary to a target sequence in a genomic nucleic acid of the infectious agent and including one or more restriction sites for the restriction endonuclease.

Embodiment 23. The method of embodiment 22, further comprising determining whether or not the infectious agent is present in the fluid sample based on a visual change detected in the second chamber after opening or rupturing the openable closed end and the openable seal.

Embodiment 24. The method of any of embodiments 21-23, wherein the visual change is generated responsive to the enzyme coated beads contacting the substrate due to the restriction endonuclease cleaving at the restriction site and releasing the enzyme coated beads from the inner side walls of the second chamber; and wherein the cleaving by the restriction enzyme occurs responsive to the single stranded oligonucleotide hybridizing with a complementary sequence in a nucleic acid of the infectious agent present in the sample.

Embodiment 25. The method of any of embodiments 21-24, wherein the sample is saliva, sweat, mucous, or blood.
Embodiment 26. The method of any of embodiments 21-25, wherein the infectious agent is a virus.
Embodiment 27. The method of any of embodiments 21-26, wherein the infectious agent is a coronavirus.
Embodiment 28. A kit comprising the device of any one of embodiments 1 or 12.
Embodiment 29. The kit of embodiment 25, comprising instructions for using the device.
Embodiment 30. A method comprising: providing a fluid sample from a subject, detecting the presence of a target nucleic acid of an infectious agent in the fluid sample utilizing the device of any of embodiments 1-11 or any of embodiments 12-21, and optionally, treating the subject with a therapeutic agent.
Embodiment 31. The method of embodiment 30, wherein the sample is saliva.
Embodiment 32. The method of embodiment 31 or 32, wherein the infectious agent is a coronavirus.

Example: SARS-CoV-2 Detection

To rapidly detect target viral RNAs, the ability of the restriction enzyme AvaII can be leveraged to cleave DNA/RNA heteroduplexes. Microbeads can be covalently linked to a solid substrate using a ssDNA bridge. The ssDNA bridge can have a sequence that is complementary to a target viral RNA and will be chosen to include at least one restriction site for AvaII. Note that there are twenty-four AvaII restriction sites in the SARS-CoV-2 genome. The microbeads can also be covalently conjugated to numerous copies of β-galactosidase or catalase or any reporter enzyme (alkaline phosphatase, peroxidase) and aqueous AvaII will be added on top of the solid substrate. If target viral RNA is introduced to the solution with the beads, it can hybridize to the ssDNAs which connect the beads to the solid substrate. Since AvaII cleaves DNA/RNA heteroduplexes but not ssDNA, the enzyme can cleave the heteroduplexes formed by the ssDNA linkers and the viral RNA. Once the DNA/RNA heteroduplexes undergo cleavage, the beads can freely diffuse away from the solid substrate. At the opposite end of the chamber with the beads, there can be a polymeric mesh with covalently linked to hydrogen peroxide or 6-Chloro-3-indolyl-3-D-galactopyranoside (Red-Gal) or any suitable substrate. When the beads diffuse across the chamber, their β-galactosidase enzymes will catalyze the formation of a red indole dye which will serve as the colorimetric readout for a positive nanoSplash test result. If target viral RNA is not present, the beads will remain linked to the solid substrate and therefore not cleave the Red-Gal. As a result, the red dye will not form, giving a negative test result. This mechanism can facilitate diagnosis of viral infection.

The nanoSplash system can be housed in a cylinder with two compartments. The first compartment can contain a solution of proteinase K to inactivate any DNases in the saliva sample and of the RNase inhibitor diethyl pyrocarbonate (DEPC) to inactivate any protease-resistant RNases in the sample. Further, a valve may be opened or a seal may be broken, allowing the contents of the first compartment to move into the second compartment. The second compartment includes the beads on the solid substrate, the polymer mesh with the Red-Gal, and a solution of AvaII and the irreversible proteinase K inhibitor MeOSuc-AAPF-CMK (Sigma Aldrich #539470). The proteinase K inhibitor in the second chamber will prevent the proteinase K from digesting AvaII or β-galactosidase. The process may work as follows: the user will place a saliva sample into the first compartment via a sample entry port, wait for first duration (e.g., 10 minutes), open or rupture seal to flow contents from first compartment into second compartment and finally wait for a second duration (e.g., at least 5 minutes or until the indication appears) to obtain the colorimetric result. In this way, the user can easily carry out testing at home without the aid of a clinician or painful sample collection. Further, the volumes of the compartments may be small to minimize reagent costs.

Computational Methods

In some embodiments, molecular dynamics (MD) modeling of AvaII interaction with the ssDNA linkers to determine AvaII contribution to any false-positive cleavage. Though AvaII should not cleave ssDNA itself, the ssDNA linkers may form dsDNA secondary structures, partially dimerize with ssDNAs from the saliva, or partially dimerize with ssRNAs from the saliva. Note that AvaII has been shown to cleave dsDNA under certain conditions. Furthermore, even weak dimerization with partially complementary ssRNAs around the location of the AvaII cut site may result in false-positive cutting. Finally, the optimal temperature for AvaII can be altered to increase cutting specificity. MD simulation of AvaII's interactions with several types of substrates at non-optimal temperatures can facilitate a useful understanding of false positives and false negative and can enable better insights to circumvent these test results.

The MD simulations for nanoSplash can include, e.g., (1) a model of AvaII binding to a target sequence DNA/RNA heteroduplex, (2) a model of AvaII binding to a nontarget sequence DNA/RNA heteroduplex, (3) a model of AvaII binding to a target dsDNA sequence, and (4) a model of AvaII binding to a nontarget dsDNA sequence. The simulations can be run at temperatures of 20° C. to mimic typical conditions during handling and 37° C. (which is the optimal temperature for AvaII). The first model will establish how AvaII binds to its optimal target sequence at 20° C. and 37° C. The second, third, and fourth models will allow visualization of AvaII's binding, partial binding, or complete lack of binding to non-optimal target nucleic acids. As mentioned, these models will help to establish reasons for false-positive results if any arise. Furthermore, if AvaII experiences non-specific activity or major inefficiency at the non-optimal temperature, the MD simulations may help identify possible ways to mutate the enzyme such that it could better operate under the non-optimal temperature conditions.

Target Sequence in SARS-CoV-2

The compositions and methods provided herein can be used to identify the presence of SARS-CoV-2 in a sample. The nucleic acid can be designed to target one or more coronavirus gene sequences. For example, a 113 bp sequence located in the E gene region of the SARS-CoV-2 genome can be targeted (World Health Organization). This sequence is as follows: 5'-ACAGGTACGTTAATAGT-TAATAGCGTACTTCTTTTTCTTGCTTTCGTGGTAT-TCTTGC TAGTTACACTAGCCATCCTTACTGCGCTTC-GATTGTGTGCGTACTGCTGCAATAT-3' (SEQ ID NO: 1). The oligonucleotide itself will need to contain the reverse complement of the above target sequence to base pair with the viral RNAs. The sequence of the oligonucleotide linker itself (which can bridge the solid substrate and the enzyme-decorated beads) can be as follows: 5'-ATAT-TGCAGCAGTACGCACACAATCGAAGCGCAGTAA-GGATGGCTAGTGTAAC TAGCAAGAATAC-CACGAAAGCAAGAAAAAGAAGTACGCTATTAACT-ATTAACGT ACCTGT-3' (SEQ ID NO: 2). In some examples, this sequence can also be flanked by short (e.g., at least 3, 4, 5, 6, 7, 8, 9, 10, 11, 12, 13, 14, 15, 16, 17, 18, 19, or 20 base pairs) oligonucleotide linker sequence attached to the 5' end and/or the 3' end of the single stranded oligonucleotide sequence. In some examples, Biotin or other modifications can be added to the 5'- or 3'-ends of an oligo using either a C6 or TEG (tetra-ethyleneglycol, 15 atom) spacer arm. Further, in some examples, a primary amino group can be used to attach a variety of modifiers (such as fluorescent dyes) to an oligonucleotide or used to attach an oligonucleotide to a solid surface. Amino modifiers can be positioned at the 5'-end with either a C6 or longer (C12) spacer arm. Amino modifications can be positioned at the 3'-end.

Non-limiting examples of single stranded oligonucleotide sequences that may be included in the nucleic acid capture portion of the device for identifying the genomic nucleic acid of SARS-CoV-2 or fragment thereof are shown below at table 1. In exemplary embodiments, SEQ ID Nos: 3, 4, 5, 10, 11, and 12 include a biotin-TEG modification that is attached to the 5' end (5BiotinTEG) of the respective oligonucleotide, and further include an amino modifier C6 dT (3AmMC6T) at their respective 3'ends. Further, SEQ ID NO: 9 includes base modifications at base 7 and 42, where at each bases 7 and 42, the base modification is Methoxy Ethoxy Cytosine. Further, SEQ ID NO: 16 includes base modifications at bases 15 and 50, where at each base 7 and 42, the base modification is Methoxy Ethoxy Cytosine. As discussed above, SEQ ID Nos: 3-16, each include at least one restriction site for the restriction enzyme, AvaII.

TABLE 1

Single stranded oligonucleotide sequence.

| Sequence | Bases | SEQ ID NO: |
|---|---|---|
| CT GTT TTC CTT CAA GGT CCA TAA GAA AAG GCT GAG AGA CAT ATT CAA AAG TGC AA | 55 | 3 |
| CT GTT TTC CTT CAA GGT CCA TAA GAA AAG GCT GAG AGA CAT ATT CA | 46 | 4 |
| CT GTT TTC CTT CAA GGT CCA TAA GAA AAG GCT GA | 34 | 5 |

TABLE 1-continued

Single stranded oligonucleotide sequence.

| Sequence | Bases | SEQ ID NO: |
|---|---|---|
| CTG TTT TCC TTC AAG GTC CAT AAG AAA AGG CTG AGA GAC ATA TTC AAA AGT GCA A | 55 | 6 |
| CTG TTT TCC TTC AAG GTC CAT AAG AAA AGG CTG AGA GAC ATA TTC A | 46 | 7 |
| CTG TTT TCC TTC AAG GTC CAT AAG AAA AGG CTG A | 34 | 8 |
| CTG TTT CTC CTT CAA GGT CCA TAA GAA AAG GCT GAG AGA CAC ATT CAA AAG TGC AA | 56 | 9 |
| CA CAA GAC CAT GTT GAC ATA CTA GGA CCT CTT TCT GCT CAA ACT GGA ATT GCC GTT TTA | 59 | 10 |
| CA CAA GAC CAT GTT GAC ATA CTA GGA CCT CTT TCT GCT CAA ACT GGA | 47 | 11 |
| CA AGA CCA TGT TGA CAT ACT AGG ACC TCT TTC TGC TCA | 38 | 12 |
| CAC AAG ACC ATG TTG ACA TAC TAG GAC CTC TTT CTG CTC AAA CTG GAA TTG CCG TTT TA | 59 | 13 |
| CAC AAG ACC ATG TTG ACA TAC TAG GAC CTC TTT CTG CTC AAA CTG GA | 47 | 14 |
| CAA GAC CAT GTT GAC ATA CTA GGA CCT CTT TCT GCT CA | 38 | 15 |
| CAC AAG ACC ATG TTC GAC ATA CTA GGA CCT CTT TCT GCT CAA ACT GGA ACT GCC GTT TTA | 60 | 16 |

The invention claimed is:

1. A device for detecting an infectious agent in a fluid sample, the device comprising:
a first chamber including a sample receiving chamber and a collection chamber, the collection chamber including a first solution;
a second chamber including:
(i) a nucleic acid capture portion including
(a) a plurality of single stranded oligonucleotides, each of the plurality of single stranded oligonucleotides comprising a first sequence complementary to a target sequence in a genomic nucleic acid of the infectious agent and one or more restriction sites for a restriction endonuclease;
(b) a plurality of enzyme conjugated beads, each enzyme conjugated bead attached to the second chamber via one of the plurality of single stranded oligonucleotides;
(c) a readout generation portion on an inner bottom surface of the second chamber, the readout generation portion comprising a substrate of an enzyme coating the enzyme coated beads, wherein the substrate is embedded in a polymeric mesh coupled to the inner bottom surface; and
(ii) a second solution, the second solution comprising the restriction endonuclease;
and
one or more openable seals between the first chamber and the second chamber, the one or more openable seals separating the first chamber and the second chamber when sealed, and the one or more openable seals configured to allow contents from the first chamber and contents from the second chamber to mix when opened or ruptured.

2. The device of claim 1, wherein the first chamber and the second chamber are disposed in a single housing; or wherein the first chamber is disposed in a first device housing and the second chamber is disposed a second device housing, the second device housing configured as a closure unit for the first device housing.

3. The device of claim 1, wherein the sample receiving chamber has an inverted conical frustum shape with a first base diameter greater than a second base diameter, and wherein a center of the second base is offset from a center of the first base.

4. The device of claim 3, wherein a central longitudinal axis parallel to a length of the collection chamber is offset from the center of the first base of the receiving chamber and aligns with the center of the second base of the receiving chamber.

5. The device of claim 1, further comprising at least one window in the first device housing for viewing a visual indication generated by the readout generation portion.

6. The device of claim 5, wherein the visual indication is a colorimetric change or a turbidimetric change, or a combination thereof.

7. The device of claim 1, wherein the fluid sample is a bodily fluid of a subject and wherein the infectious agent is selected from the group consisting of viruses, bacteria, archaea, fungi, and yeast.

8. The device of claim 1, wherein the infectious agent is selected from a group consisting of a virus, an RNA virus, and a coronavirus.

9. The device of claim 1, wherein the restriction endonuclease is selected from the group consisting of AvaII, AvrII, BanI, HaeIII, HinfI, and TaqI.

10. The device of claim 1, wherein an inner side wall of the second chamber comprises the nucleic acid capture portion.

11. The device of claim 1, wherein the first solution comprises a proteinase enzyme; and wherein the second solution further comprises a proteinase inhibitor.

* * * * *